United States Patent
Loury et al.

(10) Patent No.: US 8,748,468 B2
(45) Date of Patent: Jun. 10, 2014

(54) MANUFACTURE, COMPOSITIONS AND USES OF COAGULATION FACTOR VIIA MODULATOR

(71) Applicant: Pharmacyclics, Inc., Sunnyvale, CA (US)

(72) Inventors: David Loury, San Jose, CA (US); Tarak Mody, Sunnyvale, CA (US)

(73) Assignee: Pharmacyclics, Inc., Sunnyvale, CA (US)

( * ) Notice: Subject to any disclaimer, the term of this patent is extended or adjusted under 35 U.S.C. 154(b) by 0 days.

(21) Appl. No.: 13/668,167

(22) Filed: Nov. 2, 2012

(65) Prior Publication Data

US 2013/0158089 A1 Jun. 20, 2013

Related U.S. Application Data

(63) Continuation of application No. 12/738,372, filed as application No. PCT/US2008/080221 on Oct. 16, 2008, now Pat. No. 8,552,046.

(60) Provisional application No. 60/980,386, filed on Oct. 16, 2007.

(51) Int. Cl.
- *A01N 43/52* (2006.01)
- *A61K 31/415* (2006.01)
- *A01N 37/52* (2006.01)
- *A61K 31/155* (2006.01)
- *A01N 33/18* (2006.01)
- *A01N 33/24* (2006.01)
- *A61K 31/045* (2006.01)
- *A61K 31/04* (2006.01)

(52) U.S. Cl.
USPC .......... 514/394; 514/637; 514/728; 514/741

(58) Field of Classification Search
None
See application file for complete search history.

(56) References Cited

U.S. PATENT DOCUMENTS

| | | | |
|---|---|---|---|
| 6,867,200 B1 | 3/2005 | Allen et al. | |
| 7,479,502 B2 | 1/2009 | Kolesnikov et al. | |
| 8,299,110 B2 | 10/2012 | Kolesnikov et al. | |
| 8,415,328 B2 | 4/2013 | Dickman et al. | |
| 2003/0114457 A1 | 6/2003 | Hu et al. | |
| 2005/0176797 A1 | 8/2005 | Hu et al. | |
| 2005/0203094 A1 | 9/2005 | Kolesnikov et al. | |
| 2006/0205942 A1 | 9/2006 | Kolesnikov et al. | |
| 2007/0049523 A1* | 3/2007 | Hansen et al. ................. | 514/12 |
| 2008/0275250 A1 | 11/2008 | Dickman et al. | |
| 2009/0054432 A1 | 2/2009 | Kolesnikov et al. | |
| 2010/0298396 A1 | 11/2010 | Loury | |
| 2011/0207939 A1 | 8/2011 | Dickman | |
| 2011/0269806 A1 | 11/2011 | Kolesnikov et al. | |

FOREIGN PATENT DOCUMENTS

| | | |
|---|---|---|
| RU | 2297216 | 4/2007 |
| WO | WO-2000-035886 A2 | 6/2000 |
| WO | WO-2000-035886 A3 | 6/2000 |
| WO | WO-2002-014274 A1 | 2/2002 |
| WO | WO-2002-014307 A1 | 2/2002 |
| WO | WO-2003-006011 A1 | 1/2003 |
| WO | WO-2003-006670 A2 | 1/2003 |
| WO | WO-2003-006670 A3 | 1/2003 |
| WO | WO-2003-068756 A1 | 8/2003 |
| WO | WO-2004-050637 A2 | 6/2004 |
| WO | WO-2004-050637 A3 | 6/2004 |
| WO | WO-2004-062661 A1 | 7/2004 |
| WO | WO-2005-118554 | 12/2005 |
| WO | WO-2005-121102 A2 | 12/2005 |
| WO | WO-2005-121102 A3 | 12/2005 |
| WO | WO 2005118554 A2 * | 12/2005 |
| WO | WO-2009-052323 A2 | 4/2009 |
| WO | WO-2009-052323 A3 | 4/2009 |

OTHER PUBLICATIONS

Cancer, http://www.hlm.nih.gove/medlineplus/cancer.html, 2009, [retrieved from the Internet on Mar. 17, 2009].
EA201000633 Office Action mailed May 16, 2012.
EP08839610.6 EP Search Report dated Mar. 7, 2011.
Golub et al. "Molecular Classification of Cancer: Class Discovery and Class Prediction by Gene Expression Monitoring." *Science*, 1999, 286:521-537.
Katz et al. "A novel serine protease inhibition motif involving a multi-centered short hydrogen bonding network at the active site." *J. Mol. Biol*, 2001, 307(5):1451-1486.

(Continued)

*Primary Examiner* — James D Anderson
*Assistant Examiner* — Stephanie Springer
(74) *Attorney, Agent, or Firm* — Wilson, Sonsini, Goodrich & Rosati

(57) ABSTRACT

Treatment of cancer and thromboembolic disorders using inhibitors of Factor VIIa are disclosed herein using a compound of Formula I:

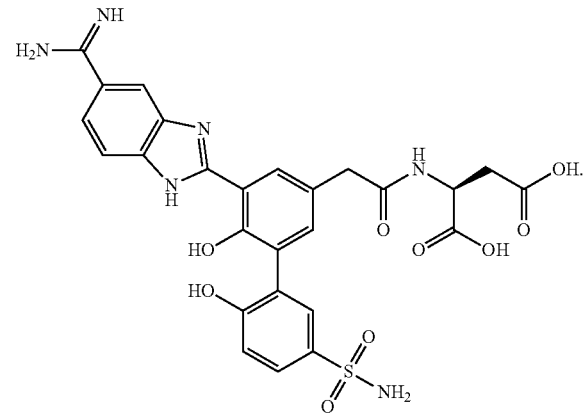

Formula I

4 Claims, 11 Drawing Sheets

(56) References Cited

OTHER PUBLICATIONS

Katz et al. "Engineering inhibitors highly selective for the S1 sites of Ser190 trypsin-like serine protease drug targets." *Chem. Biol.*, 2001, 8(11):1107-1121.
Kolesnikov et al. STN International HCAPLUS database, (Columbus, OH), Accession No. 2004:610079.
Kolesnikov et al. STN International HCAPLUS database, (Columbus, OH), Accession No. 2004:493686.
Lala et al. "Role of Nitric Oxide in Tumor Progression: Lessons from Experimental Tumors." *Cancer Metastasis Reviews*, 1998, 17(1):91-106.
Loury et al. STN International HCAPLUS database, (Columbus, OH), Accession No. 2009:486977.
PCT/US2003/038635 Search Report mailed Sep. 2, 2004.
PCT/US2005/019394 International Search Report dated Jan. 16, 2006.
PCT/US2005/019394 IPRP dated Dec. 4, 2006.
PCT/US2008/080221 Written Opinion dated Jul. 29, 2009.
PCT/US2008/080221 International Search Report dated Jul. 29, 2009.
PCT/US2008/080221 IPRP dated Apr. 20, 2010.
Sausville et al. "Contributions of Human Tumor Xenografts to Anti-cancer Drug Development." *Cancer Res*, 2006, 66(7):3351-3354.
Sendzik et al. "Environmentally friendly and efficient: iron-mediated reduction of 3-methyl-5-aryl-1,2,4-oxadiazoles to benzamidines." *Tetrahedron Lett.*, 2003, 44(48):8697-8700.
Stella "Chemical and physical bases determining the instability and incompatibility of formulated injectable drugs." *J. Parenteral Sci. Tech.*, 1996, 40(4):142-163.
Verner et al. "Development of serine protease inhibitors displaying a muticentered shor (<2.3.ANG.) hydrogen bond binding mode: Inhibitors of urokinase-type plasminogen activator and factor Xa." *J. Med. Chem.*, 2001, 44:2753-2771.
Young et al. "Optimization of a screening lead for factor VIIa/TF." *Bioorg. Med. Chem. Ltrs.*, 2001, 11(17):2253-2256.
U.S. Appl. No. 13/623,578 Final Office Action mailed Oct. 31, 2013.
U.S. Appl. No. 13/623,578 Office Action mailed Jul. 26, 2013.
U.S. Appl. No. 13/607,402 Office Action mailed Sep. 25, 2013.
Remington: Essentials of Pharmaceutics, Chapter 26, Parenteral Preparation, Pharmaceutical Press: 2013, pp. 495-532.
Sigma-Aldrich, BioUltra Biological Buffers, pp. 1-8, retrieved on Dec. 12, 2013: http://www.sigmaaldrich.come/lifescience/metabolomics/bioultra-reagents/biological-buffers.html.
Ugwu, et al. The Effects of Buffers on Protein Conformational Stability, Pharmaceutical Technology, Mar. 2004, pp. 86-113.

* cited by examiner

Uses of Compound of Formula I in Lung Colonization by B16F10 Melanoma Cells in Mice Compound of Formula I as an Inhibitor of Lewis Lung Carcinoma Tumor Growth in C57BL Mice Compound of Formula I as an Inhibitor of Lewis Lung Carcinoma Tumor Growth in C57BL Mice Compound of Formula I Showing FVIIa-induced IL-8 Response in MDA-MB-231 Human Breast Cancer Cells Subcutaneous Bioavailability of Compound of Formula I in Cynomolgus Monkeys Concentrations of Compound of Formula I following Subcutaneous Administration in Rabbits IHC Data for Tissue Factor Over Expressing in Tumors Factor VII / Factor VIIa in Primary Pancreatic Carcinoma

MANUFACTURE, COMPOSITIONS AND USES OF COAGULATION FACTOR VIIA MODULATOR

CROSS REFERENCE

This application is a continuation application of U.S. patent application Ser. No. 12/738,372, filed Apr. 16, 2012, which is a U.S. National Stage entry of international patent application PCT/US08/80221, filed Oct. 16, 2008, which claims priority from U.S. provisional patent application 60/980,386, filed Oct. 16, 2007, all of which are incorporated herein by reference in its entirety.

FIELD OF THE INVENTION

Described herein are compositions and methods for the treatment of proliferative disorders, including cancer, and thromboembolic disorders by inhibiting coagulation Factor VIIa and/or the TF:Factor VIIa complex.

BACKGROUND OF THE INVENTION

The main role of factor VII (FVII) is to initiate the process of coagulation in conjunction with tissue factor (TF). Once bound to TF, FVII is activated to FVIIa.

In cancer, the TF-FVIIa complex is found in abundance in pancreatic, gastric, breast, lung, prostate, ovarian, and colon tumors, and triggers a host of physiologic processes that facilitate angiogenesis, tumor growth, and invasion Inhibitors of Factor VIIa block tumor growth and metastasis, as has been shown in animal models.

SUMMARY OF THE INVENTION

Described herein are compositions of a compound of Formula I dissolved in water (other pharmaceutically-acceptable organic solvents are optional), in which the compositions have a pH between about 8.0 and 9.5. The pH is optionally obtained by addition of a base and/or a buffer. Additional optional components in the composition are anti-crystallizing agents. Such compositions are in the form of a non-viscous aqueous solution within 15° C. of ambient (or room) temperature, including within 10° C. of room temperature, and including within 5° C. of room temperature. Thus, at or around room temperature, such compositions are readily administrable subcutaneously to a human patient, e.g., via a narrow bore needle. As such, the viscosity and pH of the composition is such that it is suitable for subcutaneous administration to a human patient without causing irritation or other undesired side effects. In some embodiments, the viscosity of the composition increases as the temperature is decreased from room temperature. Further, upon refrigeration (broadly described as including any means for cooling the composition), such compositions form a thickened composition, including a gel composition (i.e., viscosity at least 1000 cps; in some embodiments, at least 2500 cps; in some embodiments, at least 5000 cps; and in some embodiments, at least 10,000 cps). In such a thickened form, the composition is more stable to degradation than in the unthickened form, and the compound of Formula I remains dissolved (i.e., does not precipitate or crystallize out of solution). Further, upon removing the composition from refrigeration, the composition re-forms the unthickened solution in which the compound of Formula I remains dissolved (i.e., suitable for subcutaneous administration through a narrow bore needle). In some embodiments, shaking or other forms of agitation is used to accelerate this phase transition. Further, such compositions optionally form the thickened formulation and unthickened solution reversibly as needed, by adjusting the temperature of the composition. As such, such compositions of a compound of Formula I retain their use as subcutaneously-administered formulations at or around room temperature while having long-term storage and stability upon refrigeration (in the form of a non-precipitated viscous solution/gel).

Disclosed herein, in some embodiments, is a composition comprising a compound of Formula I or a salt thereof dissolved in water:

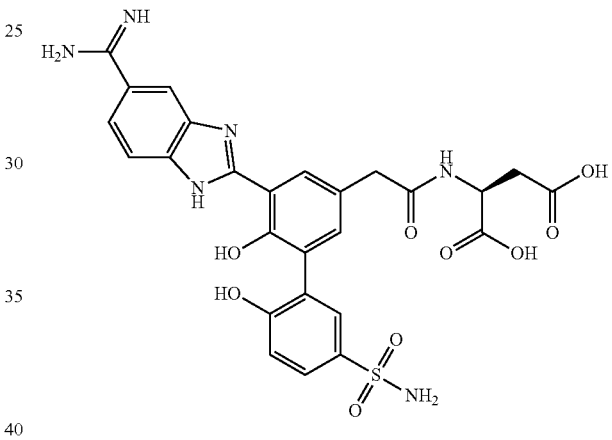

(Formula I)

having a pH between about 8.0 and about 9.5. In some embodiments, the solution has a viscosity less than 100 cps, a gel, or a solution having a viscosity greater than 100 cps. In some embodiments, the composition further comprises a base, a salt thereof, or combinations thereof. In some embodiments, the base is sodium hydroxide. In some embodiments, the composition further comprises a buffer. In some embodiments, the buffer is alkali phosphates, or salts of organic acids, inorganic acids or amino acids. In some embodiments, the buffer is citrate, carbonate, acetate, phosphate, triethanolamine, tromethamine, and glutamate. In some embodiments, the buffer is tromethamine. In some embodiments, the pH between about 8.0 and about 9.5. In some embodiments, the pH is between about 8.2 and 9.3. In some embodiments, the pH is between about 8.4 and 9.1. In some embodiments, the pH is between about 8.5 and 9.0. In some embodiments, the pH is between about 8.6 and 8.9. In some embodiments, the concentration of the compound of Formula I is greater than about 30 mg/mL. In some embodiments, the concentration of the compound of Formula I is greater than about 60 mg/mL. In some embodiments, the concentration of the compound of Formula I is greater than about 90 mg/mL. In some embodiments, the concentration of the compound of Formula I is about 120 mg/mL. In some embodiments, the composition is in the form of a solution. In some embodiments, the solution is an aqueous solution. In some embodiments, the composition forms a In some embodiments, the solution has a viscosity less than 100 cps, a gel, or a solution having a viscosity greater than 100 cps. at about 2° C. to about 8° C. In some embodiments, the composition reverts to a non-thickened solution when warmed to a temperature in excess of about 3° C. to 8° C. In some embodiments, the thickened solution is more resistant to degradation as compared to the un-thickened solution.

Disclosed herein, in some embodiments, is a composition comprising a base or salts thereof, and a compound of Formula I or salts thereof dissolved in water:

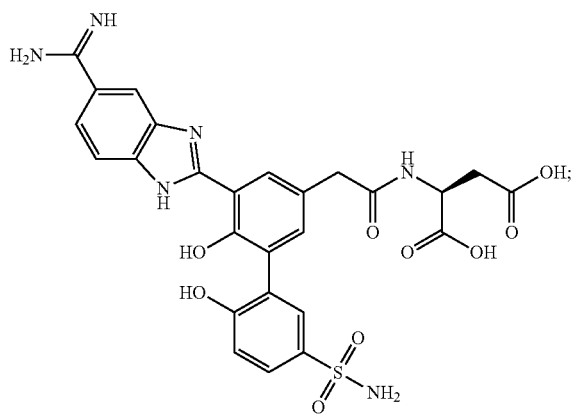

(Formula I)

wherein the composition is in the form of a solution having a pH between about 8.0 and about 9.5. In some embodiments, the solution has a viscosity less than 100 cps, a gel, or a solution having a viscosity greater than 100 cps. In some embodiments, the base is sodium hydroxide. In some embodiments, the composition further comprises a buffer. In some embodiments, the pharmaceutically acceptable buffer is alkali phosphates, or salts of organic acids, inorganic acids or amino acids. In some embodiments, the pharmaceutically acceptable buffer is citrate, carbonate, acetate, phosphate, triethanolamine, tromethamine, and glutamate. In some embodiments, the buffer is tromethamine. In some embodiments, the pH between about 8.0 and about 9.5. In some embodiments, the pH is between about 8.2 and 9.3. In some embodiments, the pH is between about 8.4 and 9.1. In some embodiments, the pH is between about 8.5 and 9.0. In some embodiments, the pH is between about 8.6 and 8.9. In some embodiments, the concentration of the compound of Formula I is greater than about 30 mg/mL. In some embodiments, the concentration of the compound of Formula I is greater than about 60 mg/mL. In some embodiments, the concentration of the compound of Formula I is greater than about 90 mg/mL. In some embodiments, the concentration of the compound of Formula I is about 120 mg/mL. In some embodiments, the composition is in the form of a solution. In some embodiments, the solution is an aqueous solution. In some embodiments, the composition forms a In some embodiments, the solution has a viscosity less than 100 cps, a gel, or a solution having a viscosity greater than 100 cps. at about 2° C. to about 8° C. In some embodiments, the composition reverts to a non-thickened solution when warmed to a temperature in excess of about 3° C. to 8° C. In some embodiments, the thickened solution is more resistant to degradation as compared to the un-thickened solution.

Disclosed herein, in some embodiments, is a composition comprising a compound of Formula I dissolved in water:

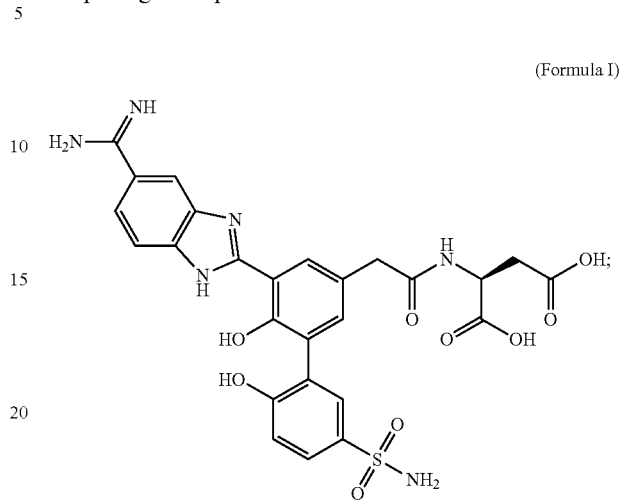

(Formula I)

and a pharmaceutically acceptable buffer wherein the composition is in the form of a solution having a pH buffer between about 8.0 and about 9.5. In some embodiments, the solution has a viscosity less than 100 cps, a gel, or a solution having a viscosity greater than 100 cps. In some embodiments, the pharmaceutically acceptable buffer is alkali phosphates, or salts of organic acids, inorganic acids or amino acids. In some embodiments, the buffer is citrate, carbonate, acetate, phosphate, triethanolamine, tromethamine, and glutamate. In some embodiments, the buffer is tromethamine. In some embodiments, the composition further comprises a base, a salt thereof, or combinations thereof. In some embodiments, the base is sodium hydroxide. In some embodiments, the pH between about 8.0 and about 9.5. In some embodiments, the pH is between about 8.2 and 9.3. In some embodiments, the pH is between about 8.4 and 9.1. In some embodiments, the pH is between about 8.5 and 9.0. In some embodiments, the pH is between about 8.6 and 8.9. In some embodiments, the concentration of the compound of Formula I is greater than about 30 mg/mL. In some embodiments, the concentration of the compound of Formula I is greater than about 60 mg/mL. In some embodiments, the concentration of the compound of Formula I is greater than about 90 mg/mL. In some embodiments, the concentration of the compound of Formula I is about 120 mg/mL. In some embodiments, the composition is in the form of a solution. In some embodiments, the solution is an aqueous solution. In some embodiments, the composition forms a In some embodiments, the solution has a viscosity less than 100 cps, a gel, or a solution having a viscosity greater than 100 cps. at about 2° C. to about 8° C. In some embodiments, the composition reverts to a non-thickened solution when warmed to a temperature in excess of about 3° C. to 8° C. In some embodiments, the thickened solution is more resistant to degradation as compared to the un-thickened solution.

Disclosed herein, in some embodiments, is a method of modulating a coagulation cascade, comprising administering to a mammal in need thereof a composition comprising a compound of Formula I dissolved in water:

(Formula I)

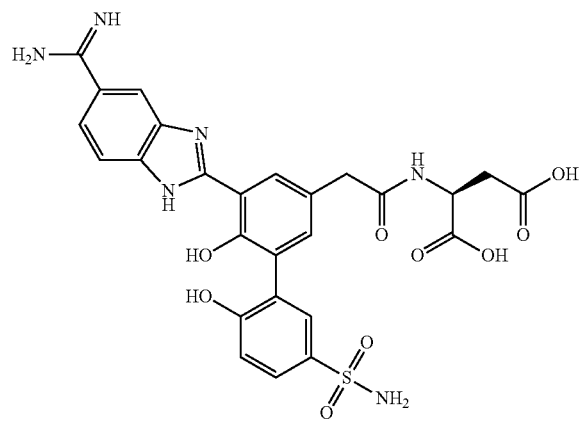

(Formula I)

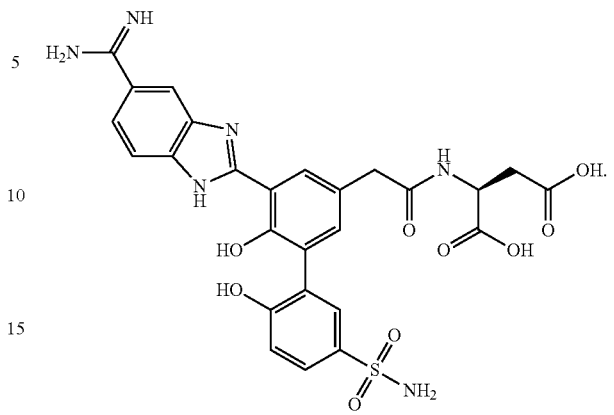

and having a pH between about 8.0 and about 9.5. In some embodiments, the solution has a viscosity less than 100 cps, a gel, or a solution having a viscosity greater than 100 cps. In some embodiments, the composition further comprises a base, a salt thereof, or combinations thereof. In some embodiments, the base is sodium hydroxide. In some embodiments, the composition further comprises a buffer. In some embodiments, the buffer is alkali phosphates, or salts of organic acids, inorganic acids or amino acids. In some embodiments, the buffer is citrate, carbonate, acetate, phosphate, triethanolamine, tromethamine, and glutamate. In some embodiments, the pH between about 8.0 and about 9.5. In some embodiments, the pH is between about 8.2 and 9.3. In some embodiments, the pH is between about 8.4 and 9.1. In some embodiments, the pH is between about 8.5 and 9.0. In some embodiments, the pH is between about 8.6 and 8.9. In some embodiments, the concentration of the compound of Formula I is greater than about 30 mg/mL. In some embodiments, the concentration of the compound of Formula I is greater than about 60 mg/mL. In some embodiments, the concentration of the compound of Formula I is greater than about 90 mg/mL. In some embodiments, the concentration of the compound of Formula I is about 120 mg/mL. In some embodiments, the composition is in the form of a solution. In some embodiments, the solution is an aqueous solution. In some embodiments, the composition forms a In some embodiments, the solution has a viscosity less than 100 cps, a gel, or a solution having a viscosity greater than 100 cps. at about 2° C. to about 8° C. In some embodiments, the composition reverts to a non-thickened solution when warmed to a temperature in excess of about 3° C. to 8° C. In some embodiments, the thickened solution is more resistant to degradation as compared to the un-thickened solution. In some embodiments, the compound of Formula I is administered subcutaneously. In some embodiments, the subcutaneous administration is accomplished by means of a syringe. In some embodiments, the gauge of the needle on the syringe is between about 20 and about 30. In some embodiments, the method further comprises administering radiation therapy to the mammal. In some embodiments, the method further comprises administering an additional chemotherapeutic agent to the mammal. In some embodiments, the mammal is human. In some embodiments, the mammal is not a human.

Disclosed herein, in some embodiments, is a method of treating a cancer and/or a thromboembolic disorder, comprising administering to a mammal in need thereof a composition comprising compound of Formula I dissolved in water:

Disclosed herein, in some embodiments, is a method of modulating tumor angiogenesis, comprising administering to a mammal in need thereof a composition comprising a compound of Formula I dissolved in water:

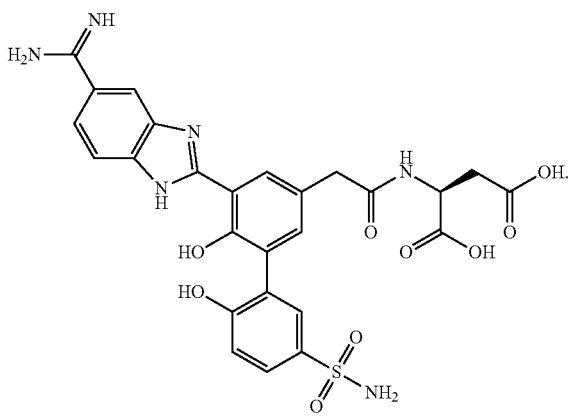

(Formula I)

and having a pH between about 8.0 and about 9.5. In some embodiments, the solution has a viscosity less than 100 cps, a gel, or a solution having a viscosity greater than 100 cps. In some embodiments, the composition is administered at a tumor site. In some embodiments, the composition further comprises a base, a salt thereof, or combinations thereof. In some embodiments, the base is sodium hydroxide. In some embodiments, the composition further comprises a buffer. In some embodiments, the buffer is alkali phosphates, or salts of organic acids, inorganic acids or amino acids. In some embodiments, the buffer is citrate, carbonate, acetate, phosphate, triethanolamine, tromethamine, and glutamate. In some embodiments, the pH between about 8.0 and about 9.5. In some embodiments, the pH is between about 8.2 and 9.3. In some embodiments, the pH is between about 8.4 and 9.1. In some embodiments, the pH is between about 8.5 and 9.0. In some embodiments, the pH is between about 8.6 and 8.9. In some embodiments, the concentration of the compound of Formula I is greater than about 30 mg/mL. In some embodiments, the concentration of the compound of Formula I is greater than about 60 mg/mL. In some embodiments, the concentration of the compound of Formula I is greater than about 90 mg/mL. In some embodiments, the concentration of the compound of Formula I is about 120 mg/mL. In some embodiments, the composition is in the form of a solution. In some embodiments, the solution is an aqueous solution. In some embodiments, the composition forms a In some embodiments, the solution has a viscosity less than 100 cps, a gel, or a solution having a viscosity greater than 100 cps. at about 2° C. to about 8° C. In some embodiments, the composition reverts to a non-thickened solution when warmed to a temperature in excess of about 3° C. to 8° C. In some embodiments, the thickened solution is more resistant to degradation as compared to the un-thickened solution. In some embodiments, the compound of Formula I is administered subcutaneously. In some embodiments, the subcutaneous administration is accomplished by means of a syringe. In some embodiments, the gauge of the needle on the syringe is between about 20 and about 30. In some embodiments, the method further comprises administering radiation therapy to the mammal. In some embodiments, the method further comprises administering an additional chemotherapeutic agent to the mammal. In some embodiments, the mammal is human. In some embodiments, the mammal is not a human.

Disclosed herein, in some embodiments, is a method of modulating the coagulation cascade, comprising administering to a mammal a modulator of Factor VIIa wherein the ratio of $C_{max}$, expressed as $\square$g/ml, to $AUC_{(0-\infty)}$, expressed as $\square$g/ml, for the modulator of the Factor VIIa is less than about 1:15. In some embodiments, the modulator of Factor VIIa is administered in the form of a solution. In some embodiments, the solution is an aqueous solution. In some embodiments, the modulator of Factor VIIa is administered subcutaneously. In some embodiments, the modulator of Factor VIIa has a molecular weight less than 1000 amu. In some embodiments, the modulator of Factor VIIa has the structure of Formula I:

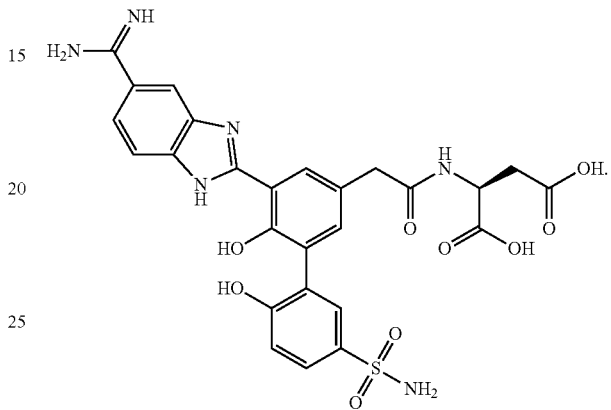

(Formula I)

Disclosed herein, in some embodiments, is a method of formulating a composition comprising a compound of Formula I, comprising mixing an aqueous solution of a compound of
Formula I:

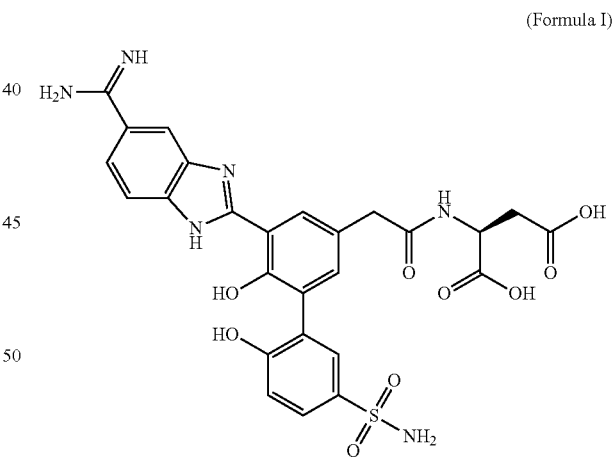

(Formula I)

with a buffer and one or more pH adjusting agents and adjusting the pH of the composition until the pH of the composition is between about 8.0 and 9.5. In some embodiments, the buffer is alkali phosphates, or salts of organic acids, inorganic acids or amino acids. In some embodiments, the buffer is citrate, carbonate, acetate, phosphate, triethanolamine, tromethamine, and glutamate. In some embodiments, the buffer is tromethamine. In some embodiments, the pH adjusting agent is a base, an acid, or combinations thereof. In some embodiments, the base is a solution of sodium hydroxide. In some embodiments, the normality of the sodium hydroxide is about 2N. In some embodiments, the acid is a solution of hydrochloric acid. In some embodiments, the normality of the hydrochloric acid is about 1N. In some embodiments, the concentration of the compound of Formula I is greater than about 30 mg/mL. In some embodiments, the concentration of the compound of Formula I is greater than about 60 mg/mL. In some embodiments, the concentration of the compound of Formula I is greater than about 90 mg/mL. In some embodiments, the concentration of the compound of Formula I is about 120 mg/mL. In some embodiments, the pH is between about 8.2 and 9.3. In some embodiments, the pH is between about 8.4 and 9.1. In some embodiments, the pH is between about 8.5 and 9.0. In some embodiments, the pH is between about 8.6 and 8.9.

Disclosed herein, in some embodiments, is a device for administering a composition comprising a compound of Formula I dissolved in water:

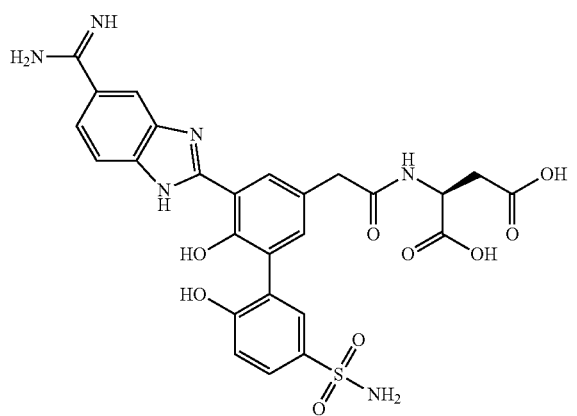

(Formula I)

and having a pH between about 8.0 and about 9.5.; and wherein the device comprises a syringe. In some embodiments, the gauge of the needle on the syringe is between about 20 and about 30. Disclosed herein, in some embodiments, is a composition has a pH between about 8.0 and about 9.5. Disclosed herein, in some embodiments, is a pH is between about 8.2 and 9.3. Disclosed herein, in some embodiments, is a pH is between about 8.4 and 9.1. Disclosed herein, in some embodiments, is a pH is between about 8.5 and 9.0. Disclosed herein, in some embodiments, is a concentration of the compound of Formula I is greater than about 30 mg/mL. Disclosed herein, in some embodiments, is a concentration of the compound of Formula I is greater than about 60 mg/mL. Disclosed herein, in some embodiments, is a concentration of the compound of Formula I is greater than about 90 mg/mL. Disclosed herein, in some embodiments, is a concentration of the compound of Formula I is about 120 mg/mL.

DESCRIPTION OF THE FIGURES

The features in the present disclosure are set forth with particularity in the appended claims. A better understanding of the features and advantages of the present disclosure will be obtained by reference to the following detailed description that sets forth illustrative embodiments, in which the principles described herein are utilized, and the accompanying drawings of which:

DETAILED DESCRIPTION OF THE INVENTION

Certain Definitions

Figure 1:
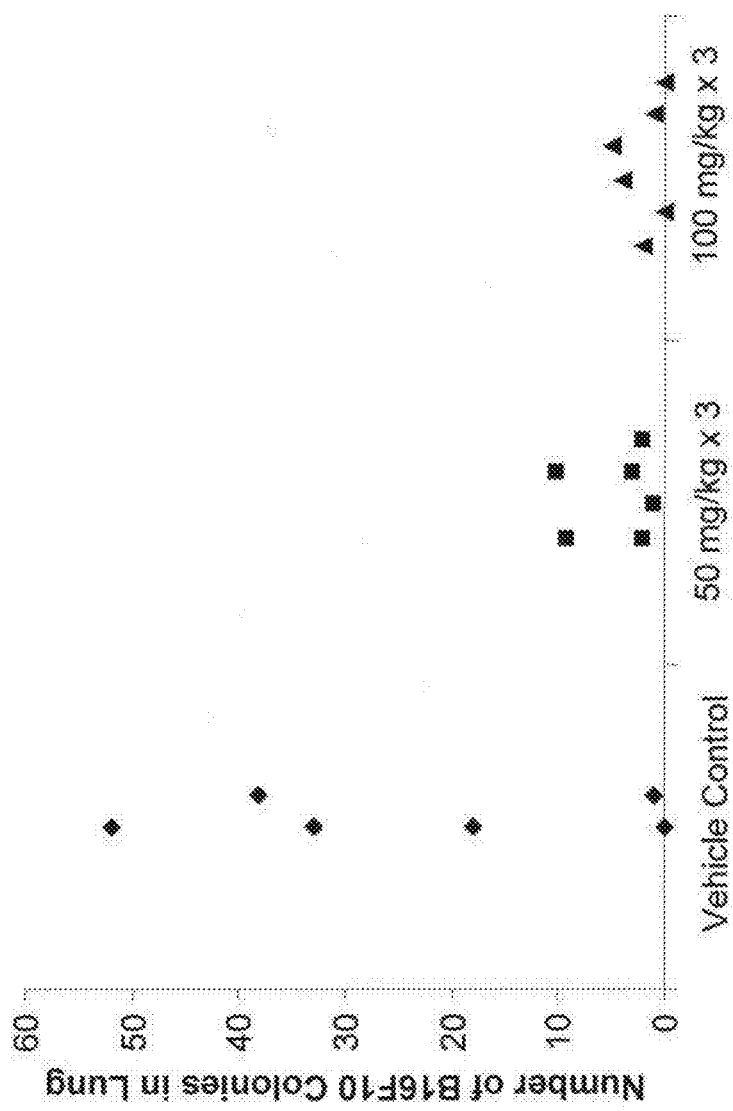
FIG. 1 presents an illustrative use of a compound of Formula I in lung colonization by Bl6F10 melanoma cells in mice.

In certain instances, Factor VII (hereinafter, "Factor VII") is a zymogen (i.e., an inactive enzyme precursor). In certain instances, FVII is converted into an active enzyme (e.g. Factor VIIa).

In certain instances, plasma coagulation factor VIIa (hereinafter, "FVIIa") is a 50 kilodalton (kDa) plasma serine protease that participates in the regulation of in vivo hemostasis. In certain instances, FVIIa is generated from FVII by the proteolysis of one or more peptide bonds.

In certain instances, Tissue Factor (also called, thromboplastin, factor III or CD 142; hereinafter, "TF") is a protein that participates in the coagulation cascade. In certain instances, TF is a receptor. In certain instances, TF comprises three domains. In certain instances, TF comprises (a) a domain that binds factor VIIa (i.e., the extracellular domain); (b) a domain which crosses the hydrophobic membrane (i.e., the transmembrane domain); and (c) a domain of 21 amino acids length inside the cell which is involved in the signaling function of TF (i.e., the cytoplasmic domain). In certain instances, TF forms a complex with FVIIa.

The term "acceptable" with respect to a composition, composition or ingredient, as used herein, means having no persistent detrimental effect on the general health of the individual being treated. By "pharmaceutically acceptable," as used herein, refers to a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

As used herein, amelioration of the symptoms of a particular disease, disorder or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

"Antioxidants" include, for example, butylated hydroxytoluene (BHT), sodium ascorbate, ascorbic acid, sodium metabisulfite and tocopherol. In certain embodiments, antioxidants enhance chemical stability where required.

"Bioavailability" refers to the percentage of the administered dose of compounds disclosed herein that becomes available in the general circulation of the animal or human being studied. The total exposure ($AUC_{(0-\infty)}$) of a drug when administered intravenously is usually defined as 100% bioavailable (F %). "Oral bioavailability" refers to the extent to which compounds disclosed herein are absorbed into the general circulation when the pharmaceutical composition is taken orally as compared to intravenous injection.

"Blood plasma concentration" refers to the concentration of compounds provided herein in the plasma component of blood of a individual. It is understood that the plasma concentration of compounds provided herein may vary significantly between individuals, due to variability with respect to metabolism and/or possible interactions with other therapeutic agents. In accordance with one embodiment disclosed herein, the blood plasma concentration of the compounds provided herein varies from individual to individual. Likewise, values such as maximum plasma concentration ($C_{max}$) or time to reach maximum plasma concentration ($T_{max}$), or total area under the plasma concentration time curve ($AUC_{(0-\infty)}$) may vary from individual to individual. Due to this variability, in some embodiments, the amount necessary to constitute "a therapeutically effective amount" of a compound provided herein varies from individual to individual.

"Carrier materials" include any commonly used excipients in pharmaceutics and should be selected on the basis of compatibility with compounds disclosed herein and the release profile properties of the desired dosage form. Carrier materials include, e.g., binders, suspending agents, disintegration agents, filling agents, surfactants, solubilizers, stabilizers, lubricants, wetting agents, diluents, and the like. "Pharmaceutically compatible carrier materials" include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like.

The term "diluent" refers to chemical compounds that are used to dilute the compound of interest prior to delivery.

"Dispersing agents," and/or "viscosity modulating agents" include materials that control the diffusion and homogeneity of a drug through liquid media. Diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol has a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose are also be used as dispersing agents. Dispersing agents useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

"Drug absorption" or "absorption" typically refers to the process of movement of drug from site of administration of a drug across a barrier into a blood vessel or the site of action, e.g., a drug moving from the gastrointestinal tract into the portal vein or lymphatic system. The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. For example, the result is reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. In another example, a "therapeutically effective amount" is that amount of a compound of Formula I which is sufficient to produce a statistically significant increase in the inhibition of Factor VIIa as determined by standard coagulation tests such as prothrombin time. In one embodiment, an appropriate "effective amount" in any individual case is determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effective amount" or "a therapeutically effective amount" varies, in some embodiments, from individual to individual, due to variation in metabolism of the compound administered, age, weight, general condition of the individual, the condition being treated, the severity of the condition being treated, and the judgment of the prescribing physician.

The terms "enhance" or "enhancing" means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system. When used in a patient, amounts effective for this use will depend on the severity and course of the disease, disorder or condition, previous therapy, the patient's health status and response to the drugs, and the judgment of the treating physician.

The term "inhibiting" includes preventing, slowing, or reversing the growth, malignancy or spread of a tumor in a patient having cancer.

The terms "kit" and "article of manufacture" are used as synonyms.

A "measurable serum concentration" or "measurable plasma concentration" describes the blood serum or blood plasma concentration, typically measured in mg, □g, or ng of therapeutic agent per ml, dl, or l of blood serum, present in the bloodstream after administration. As used herein, measurable plasma concentrations are typically measured in ng/ml or □g/ml.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "modulator" refers to a compound that alters an activity of a molecule. For example, a modulator causes an increase or decrease in the magnitude of a certain activity of a molecule compared to the magnitude of the activity in the absence of the modulator. In certain embodiments, a modulator is an modulator, which decreases the magnitude of one or more activities of a molecule. In certain embodiments, an modulator completely prevents one or more activities of a molecule. In certain embodiments, a modulator is an activator, which increases the magnitude of at least one activity of a molecule. In certain embodiments the presence of a modulator results in an activity that does not occur in the absence of the modulator.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like.

A "prodrug" refers to an agent that is converted into the parent drug in vivo. Prodrugs are often useful because, in some situations, they are easier to administer than the parent drug. They are, in some embodiments, bioavailable by oral administration whereas the parent is not. The prodrug, in some embodiments, has improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically more active form of the compound. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. In one embodiment, the prodrug is designed to alter the metabolic stability or the transport characteristics of a drug, to mask side effects or toxicity, to improve the flavor of a drug or to alter other characteristics or properties of a drug. Compounds provided herein, in some embodiments, are derivatized into suitable prodrugs. Upon in vivo administration, prodrugs of the esters of alkylcarbamic acids provided herein, such as, for example, prodrugs of compounds of Formula (I), will be metabolized to provide the parent ester of alkylcarbamic acid compound, i.e. compounds of Formula (I) will be formed upon in vivo metabolism of the prodrugs provided herein.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like. In some embodiments, the FVIIa modulator composition comprises a stabilizer. Stabilizers include but are not limited to agents that will do any of (1) improve the compatibility of excipients with a container, or a delivery system, including a syringe or a glass bottle, (2) improve the stability of a compound of Formula I (e.g. prevent degradation), or (3) improve composition stability.

"Steady state," as used herein, is when the amount of drug administered is equal to the amount of drug eliminated within one dosing interval resulting in a plateau or constant plasma drug exposure.

As used herein, the term "individual" is used to mean a mammal, including a human mammal and a non-human mammal. The terms patient, subject and individual are used interchangeably.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants are included to enhance physical stability or for other purposes.

As used herein, the term "target activity" refers to a biological activity capable of being modulated by a selective modulator. Certain exemplary target activities include, but are not limited to, binding affinity, signal transduction, enzymatic activity, tumor growth, and amelioration of one or more symptoms associated with a disease or condition.

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Other objects, features, and advantages of the methods and compositions described herein will become apparent from the following detailed description. It should be understood, however, that the detailed description and the specific examples, while indicating specific embodiments, are given by way of illustration only.

The Coagulation Cascade

Coagulation is one of the processes by which blood clots are formed. In certain instances, coagulation is initiated by injury to a blood vessel. In certain instances, platelets aggregate to seal and/or reinforce the site of injury (i.e. primary hemostasis). In certain instances, coagulation factors form fibrin strands that strengthen the aggregation of platelet (i.e. secondary hemostasis).

In certain instances, damage to a blood vessel induces the expression of a Tissue Factor (TF) gene. In certain instances, TF forms a complex with FVII. In certain instances, the binding of TF and FVII results in the activation of FVII. Active FVII is called FVIIa. In certain instances, a TF/FVIIa complex catalyzes the conversion of the inactive zymogen Factor X into an active protease, Factor Xa. In certain instances, a TF/FVIIa complex catalyzes the conversion of the inactive zymogen Factor IX into an active protease, Factor IXa. In certain instances, Factor Xa binds to Factor Va. In certain instances, a Factor IXa/Factor Va complex converts prothrombin into its active form, thrombin. In certain instances, thrombin converts fibrinogen into fibrin.

Thrombosis is the formation of a blood clot (or thrombus) inside a blood vessel. In certain instances, the formation of a thrombus obstructs the flow of blood through the circulatory system. In certain instances, the clinical manifestations of thrombosis (i.e. the formation of blood clots in a blood vessel) include acute myocardial infarction (AMI or heart attack); unstable angina (UA); and deep vein thrombosis (i.e. the formation of blood clots in lower extremities; hereinafter "DVT"). In certain instances, the formation of DVT results in the development of pulmonary embolism (PE). In certain instances, the development of a PE is fatal.

In certain instances, thrombosis occurs systemically (i.e. microclots form throughout the vascular system). Systemic thrombosis is known as disseminated intravascular coagulation (DIC). In certain instances, DIC results from a viral infection (e.g. by the Ebola virus), sepsis, and/or rheumatoid arthritis. In certain instances, DIC results in a reduction in circulating coagulation factors. In certain instances, a reduction in the number of circulating coagulation factors results in multiple organ failure, hemorrhage, and/or death.

In certain instances, the formation or embolization of blood clots in a blood vessel of the brain results in ischemic stroke. In certain instances, triggering factors that lead to stroke are atrial fibrillation or abnormal rhythm of the atria of the heart and atherosclerosis followed by thrombosis in the main artery leading from the heart to the brain (carotid artery).

In certain instances, the coagulation cascade is aberrantly activated in individuals with a cancer. In certain instances, venous thrombosis is the first indication of malignancy in an otherwise healthy individual. In certain instances, DIC develops in patients with carcinomas of the prostate, stomach, colon, breast, ovary, lung, gall bladder and in patients with melanoma. In certain instances, tumor cells shed membrane fragments that carry TF. In certain instances, tumor cells produce soluble substances that induce TF expression on host cells (e.g. endothelium and monocytes).

In certain instances, TF is aberrantly expressed on tumor cells (e.g. lung cancer cells, colorectal cancer cells, breast cancer cells, malignant melanoma cells, gliomas cells, prostate cancer cells, gastric cancer cells, and/or ovarian cancer cells). In certain instances, the aberrant expression of TF results (partially or fully) in the initiation of angiogenic signaling. In certain instances, a tumor cell's malignancy (e.g., in colorectal and breast cancer) is proportional to the level of TF expressed in the cell.

In certain instances, the aberrant expression of TF facilitates metastasis. In certain instances, metastasis involves intravasation of tumor cells from the primary tumor, survival during circulation, arrest during microcirculation, extravasation, and tumor growth at a secondary site. In certain instances, a TF/FVIIa is involved in multiple oncogenic processes required for tumor growth, angiogenesis, and tumor metastasis.

In certain instances, overexpression of TF in mouse fibrosarcoma cells results in the upregulation of a vascular endothelial growth factor (VEGF) gene and the downregulation of a thrombospondin gene. In certain instances, the upregulation of a VEGF gene and the downregulation of a thrombospondin gene result in increased vascularization of tumors. In certain instances, thrombin enhances tumor cell interactions with a blood vessel wall by upregulating cell-cell adhesion molecule 1 on endothelial cells and/or the subendothelial matrix. In certain instances, thrombin generation facilitates metastasis by altering endothelial permeability and/or by upregulating matrix degradation.

In certain instances, siRNA-mediated knock-down of TF has little or no effect on tumor cell proliferation and spheroid formation in vitro.

I. Compounds of Formula I

Described herein is a small molecule selective modulator of Factor VIIa for the treatment of a proliferative disorders (e.g., cancer), and/or a thromboembolic disorders. The structure of the small molecule modulator of Factor VIIa is (also referred herein as Formula I):

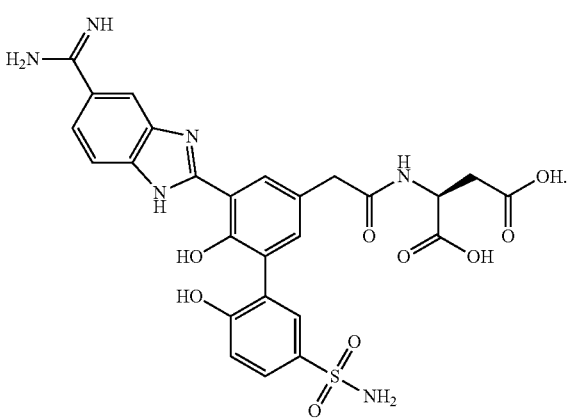 [SMILES: N=C(N)c1ccc2[nH]c(-c3cc(CC(=O)N[C@@H](CC(=O)O)C(=O)O)cc(-c4cc(S(N)(=O)=O)ccc4O)c3O)nc2c1]

For example, as shown in FIG. 1, the compound of Formula I prevents lung colonization by Bl6F10 melanoma cells in mice. In this experiment, the compound of Formula I was administered subcutaneously 1.5 h before tumor cell inoculation, and then 4.5 h and 24 h after tumor cell inoculation. In the absence of the compound of Formula I (i.e., the vehicle alone), a substantial number of colonies formed in the majority of the inoculated mice. However, following the 3× dose of 50 mg/kg of the compound of Formula I, substantially fewer colonies were formed in the mice. At the higher dose of 3×100 mg/kg, the number of colonies further dropped. As a result, in some embodiments, the compound of Formula I inhibit the metastasis of tumor cells.

Figure 2:
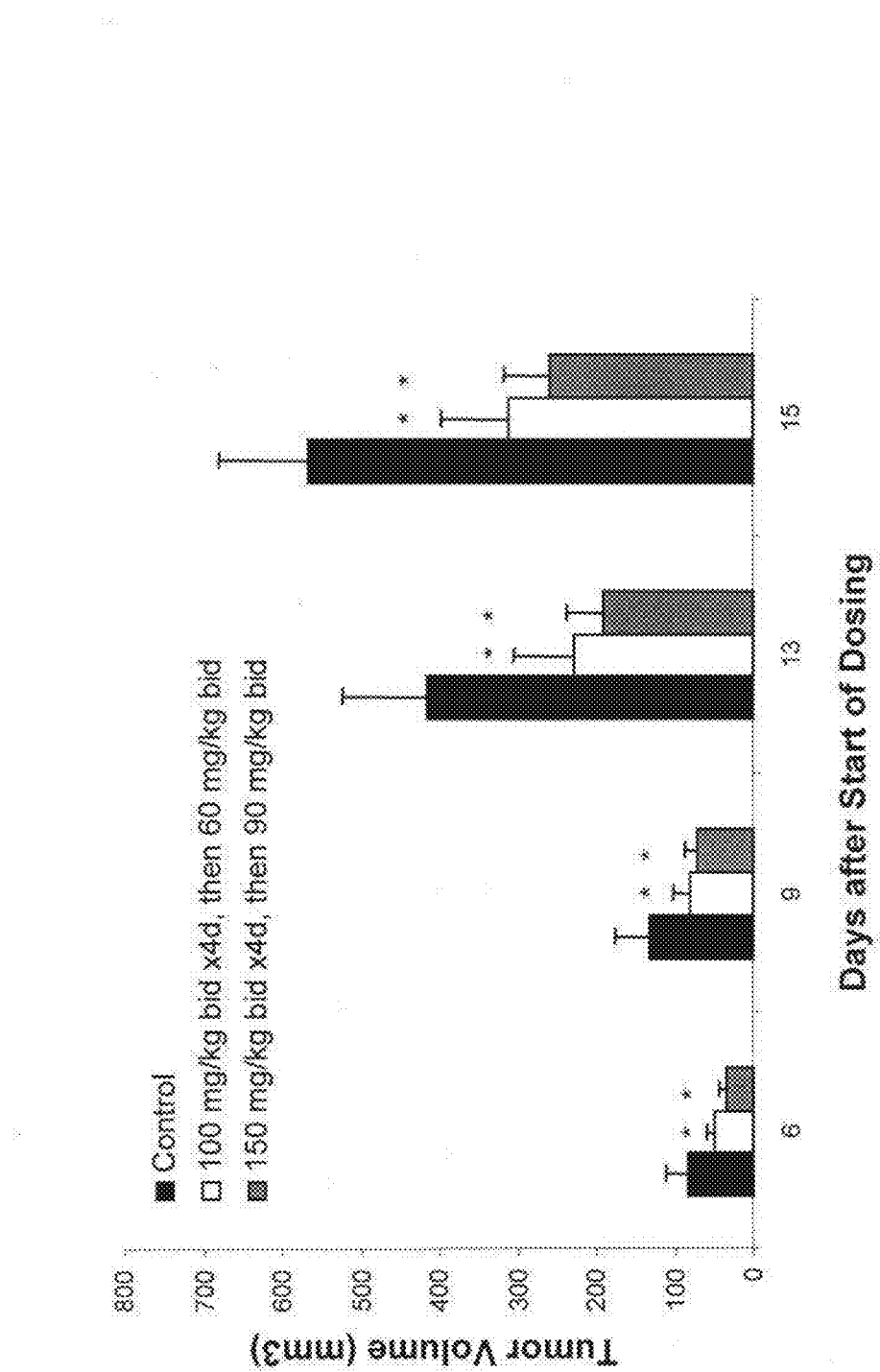
FIG. 2 presents an illustrative use of a compound of Formula I as an modulator of Lewis lung carcinoma tumor growth in C57BL mice.

In yet another example, as shown in FIG. 2, the compound of Formula I inhibits Lewis lung carcinoma tumor growth in C57BL mice. In this example, the compound of Formula I was administered subcutaneously starting 4 days after tumor cell implantation in the mice (the two different dosing schedules are described in FIG. 2). As can be seen in FIG. 2, there was at least a 50% reduction ($p<0.01$) in tumor volume, depending on the dosing schedule used. As a result, the compound of Formula I inhibits the growth of tumor cells.

Figure 3:
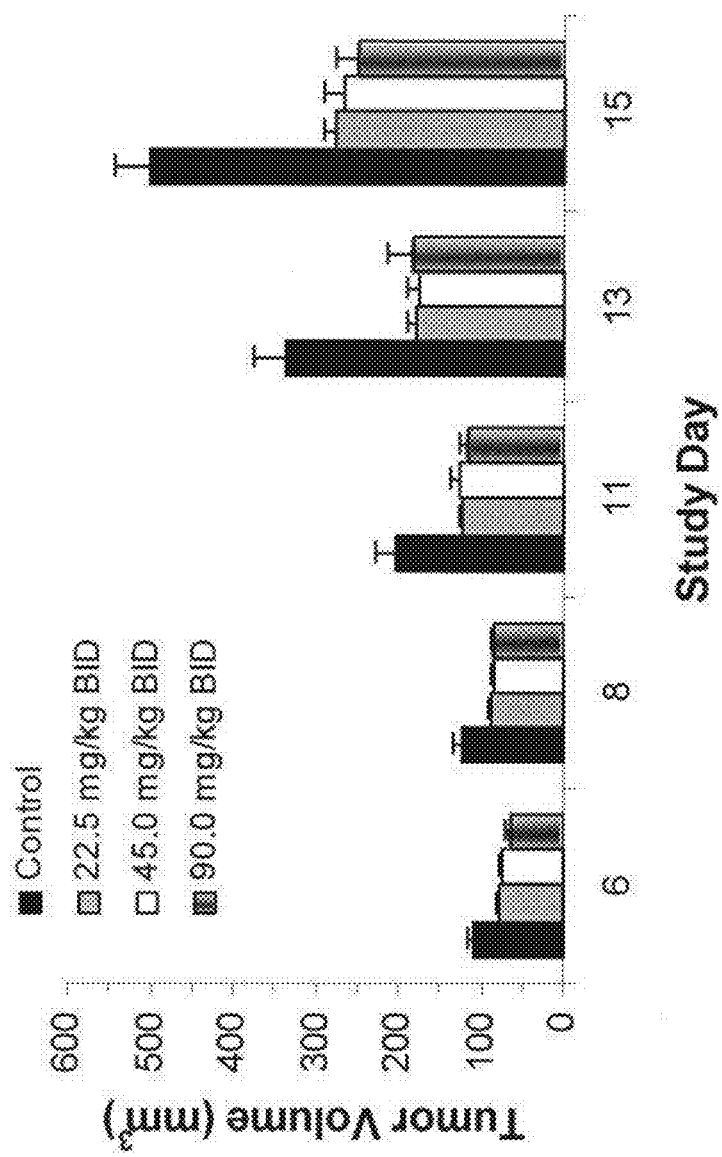
FIG. 3 presents an illustrative use of a compound of Formula I as an modulator of Lewis lung carcinoma tumor growth in C57BL mice.

In a follow-up tumor suppression study, the compound of Formula I reduced Lewis lung carcinoma tumor growth in C57BL mice by approximately 50% when given twice daily at subcutaneous doses 22.5, 45, and 90 mg/kg (FIG. 3).

Figure 4:
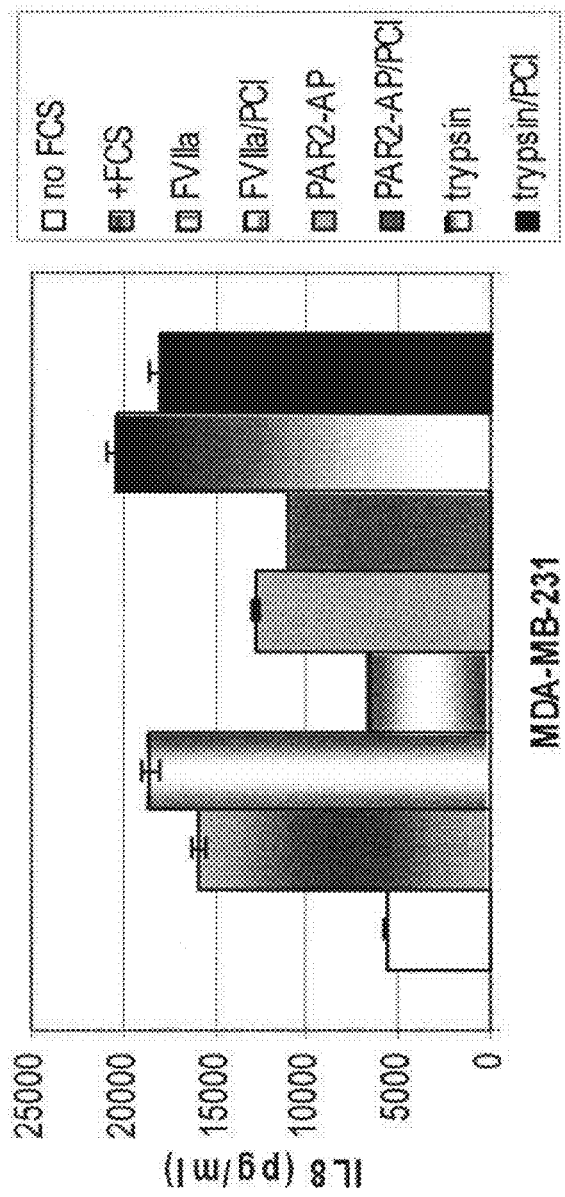
FIG. 4 presents an illustrative use of a compound of Formula I and its FVIIa-induced IL-8 response in MDA-MB-231 human breast cancer cells.

In another example, as shown in FIG. 4, MDA-MB-231 human breast cancer cells were incubated in the presence of FVIIa in vitro. Secretion of the chemokine IL-8 increased to over 3-fold of baseline. The addition of a 1 µM concentration of the compound of Formula I to the medium, completely abrogated the FVIIa-induced IL-8 response.

Figure 5:
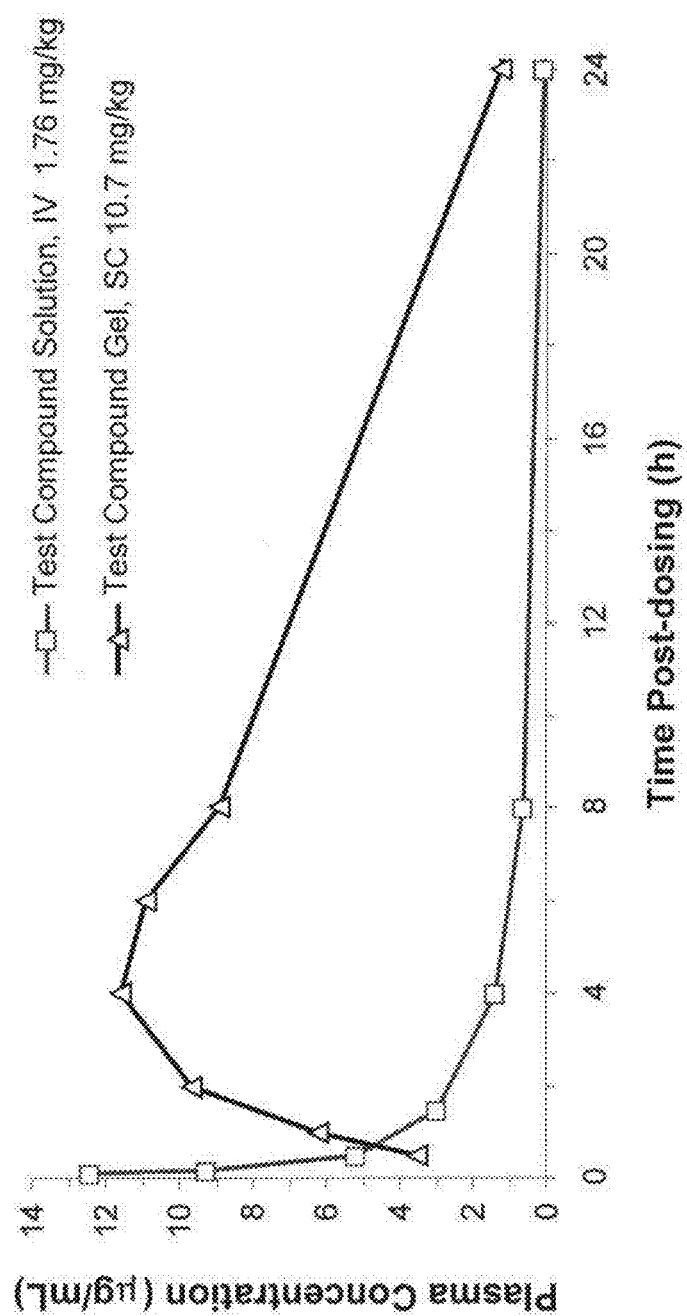
FIG. 5 presents an illustrative example of subcutaneous bioavailability of a compound of Formula I in Cynomolgus monkeys.

In yet another example, as shown in FIG. 5, a study was performed in cynomolgus monkeys with the compound of Formula I. Intravenous and subcutaneous administration was performed to determine its subcutaneous bioavailability. The subcutaneous bioavailability of the test compound following a single 10.7 mg/kg dose was estimated to be 138±33%. The relative standard deviation for systemic exposure (AUC) following subcutaneous dosing was 20.9% (n=3).

One of the aspects described herein is the use of a small molecule modulator of Factor VIIa, in particular the compound of Formula I, for the treatment of cancer. In such an aspect, a human patient having cancer is administered a pharmaceutically acceptable composition containing the compound of Formula I. Relevant primary cancers include: adrenal cortical cancer, anal cancer, bile duct cancer, bladder cancer, bone cancer, adult CNS brain tumors (including gliomas, astrocytoma, glioblastoma, oligodendroglioma, and meningioglioma), brain metastases, breast cancer, cervical cancer, childhood Non-Hodgkin's lymphoma, colon and rectum cancer, endometrial cancer, esophagus cancer, Ewing's family of tumors, eye cancer, gallbladder cancer, gastrointestinal carcinoid tumors, gastrointestinal stromal tumors, gestational trophoblastic disease, hematological malignancies, Hodgkin's disease, Kaposi'sarcoma, kidney cancer, laryngeal and hypopharyngeal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplastic syndrome, nasal cavity and paranasal cancer, nasopharyngeal cancer, neuroblastoma, oral cavity and oropharyngeal cancer, osteosarcoma, ovarian cancer, pancreatic cancer, parathyroid cancer, penile cancer, pituitary tumor, prostate cancer, retinoblastoma, rhabdomyosarcoma, salivary gland cancer, sarcoma (osteosarcoma and rhabdomyosarcoma), melanoma skin cancer, nonmelanoma skin cancer, stomach cancer, testicular cancer, thymus cancer, thyroid cancer, uterine sarcoma, vaginal cancer, vulvar cancer, and Waldenstrom's macroglobulinemia. Relevant metastatic tumors include bone metastases, brain metastases, liver metastases, lung metastases and soft tissue metastases. In one embodiment, the cancer is selected from: lung cancer, colorectal cancer, breast cancer, malignant melanoma, ovarian cancer, and pancreatic cancer.

Treatment of cancer includes inhibiting growth of the size of a tumor, inhibiting angiogenesis associated with a tumor, and/or inhibiting metastasis of a tumor.

In addition, in some embodiments, the compound of Formula I is used to treat a patient in which the activity of Factor VIIa contributes to the symptomology or severity of a disease or condition. Also, in other embodiments, the compound of Formula I is used to treat a patient in which the formation of the TF-FVIIa complex contributes to the symptomology or severity of a disease or condition. The method of treating comprises administering to the patient the compound of Formula I, which serves as an modulator of the activity of Factor VIIa.

The compositions containing the compound(s) described herein are administered for prophylactic and/or therapeutic treatments. In therapeutic applications, the compositions are administered to a patient already suffering from a disease, condition or disorder, in an amount sufficient to cure or at least partially arrest the symptoms of the disease, disorder or condition. Amounts effective for this use will depend on the severity and course of the disease, disorder or condition, previous therapy, the patient's health status and response to the drugs, and the judgment of the treating physician.

In some embodiments, in the case wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In other embodiments, in the case wherein the patient's status does improve, upon the doctor's discretion the administration of the compounds are given continuously. In further embodiments the dose of drug being administered is temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. In other embodiments, the dose reduction during a drug holiday is from about 10% to about 100%, including by way of example only about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

II. Pharmaceutical Compositions Comprising Compound I

Provided herein are pharmaceutical compositions that include a compound described herein and a pharmaceutically acceptable diluent(s), excipient(s), or carrier(s). In some embodiments, the compounds described herein are administered as pharmaceutical compositions in which compounds described herein are mixed with other active ingredients, as in combination therapy. In some embodiments, the pharmaceutical compositions include other medicinal or pharmaceutical agents, carriers, adjuvants, such as preserving, stabilizing, wetting or emulsifying agents, solution promoters, salts for regulating the osmotic pressure, and/or buffers. In other embodiments, the pharmaceutical compositions also contain other therapeutically valuable substances.

Presented herein are compositions comprising a compound of Formula I, or a salt thereof.

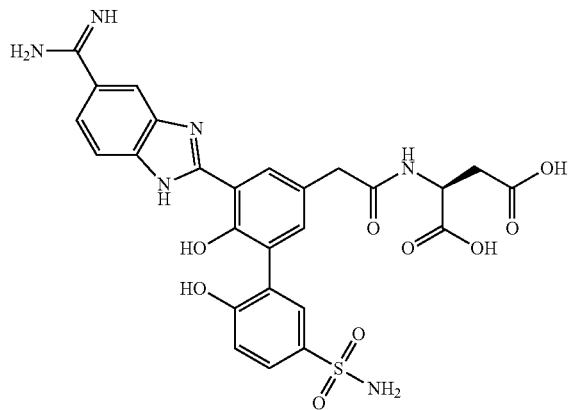

(Formula I)

In some embodiments, the composition has a concentration of a compound of Formula I between about 1 and about 100 mM. In some embodiments, the composition has a concentration of a compound of Formula I between about 10 and about 90 mM. In some embodiments, the composition has a concentration of a compound of Formula I between about 20 and about 80 mM. In some embodiments, the composition has a concentration of a compound of Formula I between about 30 and about 70 mM. In some embodiments, the composition has a concentration of a compound of Formula I between about 40 and about 60 mM. In some embodiments, the composition has a concentration of a compound of Formula I between about 50 and about 80 mM. In some embodiments, the composition has a concentration of a compound of Formula I between about 1 and about 5 mM.

In some embodiments, the concentration of the compound of Formula I is greater than about 30 mg/mL. In some embodiments, the concentration of the compound of Formula I is greater than about 60 mg/mL. In some embodiments, the concentration of the compound of Formula I is greater than about 90 mg/mL. In some embodiments, the concentration of the compound of Formula I is about 120 mg/mL.

In some embodiments, the composition further comprises a base, a salt thereof, or combinations thereof. In some embodiments, the base is sodium hydroxide.

In some embodiments, the composition further comprises a buffer. In some embodiments, the buffer is alkali phosphates, or salts of organic acids, inorganic acids or amino acids. In some embodiments, the buffer is citrate, carbonate, acetate, phosphate, triethanolamine (also known as TEA), tromethamine (also known as TRIS), and glutamate.

In some embodiments, the buffer is tromethamine. Tromethamine has the chemical formula: 2-amino-2-hydroxymethyl-1,3-propanediol. It is a mildly alkaline chemical compound that can be used to buffer a composition to a pH range from about 7 to about 9.

In some embodiments, when one or more buffers are utilized in the compositions of the present disclosure, they are combined, e.g., with a pharmaceutically acceptable vehicle and are present in the final composition, e.g., in an amount ranging from about 0.1% to about 20%, from about 0.5% to about 10%. In come embodiments, the amount of buffer is an amount such that the pH of the composition does not interfere with the body's natural buffering system. In some embodiments, the concentration of the buffer present in the composition is from about 5 mM to about 200 mM. In some embodiments, the concentration of the buffer present in the composition is from about 20 mM to about a 100 mM.

In some embodiments, the pH of the composition is such that it is suitable for subcutaneous administration to a human patient without causing irritation or other undesired side effects. In some embodiments, the pH between about 8.0 and about 9.5. In some embodiments, the pH is between about 8.2 and 9.3. In some embodiments, the pH is between about 8.4 and 9.1. In some embodiments, the pH is between about 8.5 and 9.0. In some embodiments, the pH is between about 8.6 and 8.9.

In some embodiments, the pharmaceutical compositions described herein are stable with respect to one or more of pH or compound degradation over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 1 month, at least about 2 months, at least about 3 months, at least about 4 months, at least about 5 months, or at least about 6 months. In other embodiments, the compositions described herein are stable with respect to one or more of pH or compound degradation over a period of any of at least about 1 week. Also described herein are compositions that are stable with respect to one or more of pH or compound degradation over a period of any of at least about 1 month.

In some embodiments, the composition is in the form of an aqueous solution. In some embodiments, the viscosity of the composition is such that it is suitable for subcutaneous administration to a human patient. In some embodiments, the composition is in the form of a non-viscous aqueous solution within 15° C. of ambient (i.e., room) temperature. In some embodiments, the composition is in the form of a non-viscous aqueous solution within 10° C. of room temperature. In some embodiments, the composition is in the form of a non-viscous aqueous solution within 5° C. of room temperature.

In some embodiments, the composition is a clear solution (e.g. there is no precipitate visible in the solution). In some embodiments, the color of the composition is amber.

In some embodiments, the viscosity of the composition increases as the temperature is decreased from room temperature. In some embodiments, the viscosity of the composition increases when the temperature of the composition is between about 2° C. to about 8° C. (e.g. refrigerator temperature). In some embodiments, the composition is in the form of a thickened solution (e.g., gel, a semi-solid, a paste, or a jelly). In some embodiments, the composition is more resistant to degradation (i.e., stable) when in the thickened solution as compared to the non-viscous aqueous solution. In some embodiments, a larger percentage of a compound of Formula I remains dissolved (i.e., does not precipitate or crystallize out of solution) in the thickened solution as compared to the non-viscous aqueous solution. In some embodiments, the thickened solution enables long-term storage. In some embodiments, the thickened solution has increased stability as compared to the non-viscous aqueous solution.

In some embodiments, the composition is in the form of a gel. In some embodiments, the viscosity of the composition is at least 1000 cps. In some embodiments, the viscosity of the composition is at least 2500 cps. In some embodiments, the viscosity of the composition is at least 5000 cps. In some embodiments, the viscosity of the composition is at least 10,000 cps. In some embodiments, the viscosity of the compositions presented herein is measured in any suitable manner. For example, in some embodiments, an LVDV-II+CP Cone Plate Viscometer and a Cone Spindle CPE-40 is used to calculate the viscosity of the compositions described herein.

In some embodiments, the thickened solution is an opaque semi-solid mass. In some embodiments, the color of the thickened solution is bright yellow.

In some embodiments, increasing the temperature to greater than about 2° C. to about 8° C. results in the composition reverting to a non-viscous aqueous solution (i.e., suitable for subcutaneous administration through a narrow bore needle). In some embodiments, a compound of Formula I remains dissolved in solution following reversion to a non-viscous aqueous solution. In some embodiments, the temperature is increased by any suitable manner (e.g. friction, shaking, agitation, the application of heat).

In some embodiments, the compositions described herein are readily administrable subcutaneously to a human patient. In some embodiments, the compositions described herein are readily administrable subcutaneously to a human patient by a needle with a gauge between about 20 (i.e., the nominal outer diameter is 0.902 mm) and about 33 (i.e., the nominal outer diameter is 0.203 mm). In some embodiments, the compositions described herein are readily administrable subcutaneously to a human patient by a needle with a gauge between about 22 (i.e., the nominal outer diameter is 0.711 mm) and about 31 (i.e., the nominal outer diameter is 0.254 mm). In some embodiments, the compositions described herein are readily administrable subcutaneously to a human patient by a needle with a gauge between about 24 (i.e., the nominal outer diameter is 0.559 mm) and about 29 (i.e., the nominal outer diameter is 0.330 mm). In some embodiments, the compositions described herein are readily administrable subcutaneously to a human patient by a needle with a gauge between about 25 (i.e., the nominal outer diameter is 0.508 mm) and about 27 (i.e., the nominal outer diameter is 0.406 mm).

Other Excipients

In some embodiments, the compositions described herein include excipients, other medicinal or pharmaceutical agents, carriers, adjuvants, such as preserving, stabilizing, wetting or emulsifying agents, solution promoters, and salts for regulating the osmotic pressure. In other embodiments, the excipients, carriers, adjuvants, are useful in forming a pharmaceutically acceptable thickened composition. In a further embodiment, the pharmaceutically acceptable thickened composition is in the form of a gel composition.

In some embodiments, the compositions comprise a stabilizing agent. In some embodiments, stabilizing agent is selected from, for example, fatty acids, fatty alcohols, alcohols, long chain fatty acid esters, long chain ethers, hydrophilic derivatives of fatty acids, polyvinyl pyrrolidones, polyvinyl ethers, polyvinyl alcohols, hydrocarbons, hydrophobic polymers, moisture-absorbing polymers, and combinations thereof. In some embodiments, amide analogues of stabilizers are also used. In a further embodiment, the chosen stabilizer changes the hydrophobicity of the composition (e.g., oleic acid, waxes), or improves the mixing of various components in the composition (e.g., ethanol), controls the moisture level in the formula (e.g., PVP or polyvinyl pyrrolidone), controls the mobility of the phase (substances with melting points higher than room temperature such as long chain fatty acids, alcohols, esters, ethers, amides etc. or mixtures thereof; waxes), and/or improves the compatibility of the formula with encapsulating materials (e.g., oleic acid or wax). In another embodiment some of these stabilizers are used as solvents/co-solvents (e.g., ethanol). In a further embodiment, stabilizers are present in sufficient amount to inhibit the degradation of a compound of Formula I. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Other useful compositions include one or more antioxidants to enhance chemical stability where required. Suitable antioxidants include, by way of example only, ascorbic acid and sodium metabisulfite. In one embodiment, antioxidants are selected from metal chelating agents, thiol containing compounds and other general stabilizing agents.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

In some embodiments, the composition comprises a gelling agent. Suitable gelling agents for use in preparation of the FVIIa modulator gel composition include, but are not limited to, celluloses, cellulose derivatives, cellulose ethers (e.g., carboxymethylcellulose, ethylcellulose, hydroxyethylcellulose, hydroxymethylcellulose, hydroxypropylmethylcellulose, hydroxypropylcellulose, methylcellulose), guar gum, xanthan gum, locust bean gum, alginates (e.g., alginic acid), silicates, starch, tragacanth, carboxyvinyl polymers, carrageenan, paraffin, petrolatum and any combinations or mixtures thereof. Other currently commercially-available glycerin-based gels, glycerin-derived compounds, conjugated, or crosslinked gels, matrices, hydrogels, and polymers, as well as gelatins and their derivatives, alginates, and alginate-based gels, and even various native and synthetic hydrogel and hydrogel-derived compounds are all expected to be useful in the composition of the FVIIa modulator compositions. In some embodiments, gels include, but are not limited to, alginate hydrogels SAF-Gel (ConvaTec, Princeton, N.J.), Duoderm Hydroactive Gel (ConvaTec), Nu-gel (Johnson & Johnson Medical, Arlington, Tex.); Carrasyn (V) Acemannan Hydrogel (Carrington Laboratories, Inc., Irving, Tex.); glycerin gels Elta Hydrogel (Swiss-American Products, Inc., Dallas, Tex.) and K-Y Sterile (Johnson & Johnson). In further embodiments, biodegradable biocompatible gels also represent compounds present in FVIIa modulator compositions disclosed and described herein.

In some embodiments, the composition comprises a suspending agent. Useful suspending agents include for example only, compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like. In some embodiments, useful aqueous suspensions also contain one or more polymers as suspending agents. Useful polymers include water-soluble polymers such as cellulosic polymers, e.g., hydroxypropyl methylcellulose, and water-insoluble polymers such as cross-linked carboxyl-containing polymers In some embodiments, the composition comprises an additional surfactant (co-surfactant) and/or buffering agent. In some embodiments, the surfactant and/or buffering agent is a) natural and synthetic lipophilic agents, e.g., phospholipids, cholesterol, and cholesterol fatty acid esters and derivatives thereof; b) nonionic surfactants, which include for example, polyoxyethylene fatty alcohol esters, sorbitan fatty acid esters (Spans), polyoxyethylene sorbitan fatty acid esters (e.g., polyoxyethylene (20) sorbitan monooleate (Tween 80), polyoxyethylene (20) sorbitan monostearate (Tween 60), polyoxyethylene (20) sorbitan monolaurate (Tween 20) and other Tweens, sorbitan esters, glycerol esters, e.g., Myrj and glycerol triacetate (triacetin), polyethylene glycols, cetyl alcohol, cetostearyl alcohol, stearyl alcohol, polysorbate 80, poloxamers, poloxamines, polyoxyethylene castor oil derivatives (e.g., Cremophor® RH40, Cremphor A25, Cremphor A20, Cremophor® EL) and other Cremophors, sulfosuccinates, alkyl sulphates (SLS); PEG glyceryl fatty acid esters such as PEG-8 glyceryl caprylate/caprate (Labrasol), PEG-4 glyceryl caprylate/caprate (Labrafac Hydro WL 1219), PEG-32 glyceryl laurate (Gelucire 444/14), PEG-6 glyceryl mono oleate (Labrafil M 1944 CS), PEG-6 glyceryl linoleate (Labrafil M 2125 CS); propylene glycol mono- and di-fatty acid esters, such as propylene glycol laurate, propylene glycol caprylate/caprate; Brij® 700, ascorbyl-6-palmitate, stearylamine, sodium lauryl sulfate, polyoxethyleneglycerol triiricinoleate, and any combinations or mixtures thereof; c) anionic surfactants include, but are not limited to, calcium carboxymethylcellulose, sodium carboxymethylcellulose, sodium sulfosuccinate, dioctyl, sodium alginate, alkyl polyoxyethylene sulfates, sodium lauryl sulfate, triethanolamine stearate, potassium laurate, bile salts, and any combinations or mixtures thereof; and d) cationic surfactants such as quaternary ammonium compounds, benzalkonium chloride, cetyltrimethylammonium bromide, and lauryldimethylbenzyl-ammonium chloride.

In a some embodiments, when one or more co-surfactants are utilized in the compositions of the present disclosure, they are combined, e.g., with a pharmaceutically acceptable vehicle and is present in the final composition, e.g., in an amount ranging from about 0.1% to about 20%, from about 0.5% to about 10%.

In some embodiments, the compositions described herein comprise a diluent. In some embodiments, the diluent is a salt dissolved in buffered solutions (e.g. phosphate buffered saline solution), lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, or combinations thereof.

In some embodiments, the compositions disclosed herein are isotonic. Isotonic compositions are provided by the addition of a tonicity agent. Suitable tonicity agents include, but are not limited to any pharmaceutically acceptable sugar, salt or any combinations or mixtures thereof, such as, but not limited to dextrose and sodium chloride. In further embodiments, the tonicity agents are present in an amount from about 100 mOsm/kg to about 500 mOsm/kg. In some embodiments, the tonicity agent is present in an amount from about 200 mOsm/kg to about 400 mOsm/kg, from about 280 mOsm/kg to about 320 mOsm/kg.

Useful compositions also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some embodiments, the compositions disclosed herein comprise preservatives. Suitable preservatives for use in the compositions described herein include, but are not limited to benzoic acid, boric acid, p-hydroxybenzoates, phenols, chlorinated phenolic compounds, alcohols, quaternary compounds, quaternary ammonium compounds (e.g. benzalkonium chloride, cetyltrimethylammonium bromide or cetylpyridinium chloride), stabilized chlorine dioxide, mercurials (e.g. merfen or thiomersal), or mixtures thereof. In some embodiments, the preservative is methyl paraben. In some embodiments, the methyl paraben is at a concentration of about 0.05% to about 1.0%, about 0.1% to about 0.2%.

In some embodiments, the compositions disclosed herein comprise a viscosity enhancing agent. Viscosity agents such as, but not limited to bentonite, carbomer, ceratonia, cetostearyl alcohol, chitosan, colloidal silicon dioxide, cyclomethicone, hypromellose, magnesium aluminum silicate, maltitol, maltodextrin, medium chain triglycerides, polydextrose, polyvinyl alcohol, propylene glyceryl alginate, sodium alginate, tragacanth and any combinations or mixtures thereof are suitable for use in the compositions described herein. In addition, viscous contrast agents such as iodixanol (Visipaque, Amersham Health), and sucrose-based mediums like sucrose acetate isobutyrate (SAIB) (Eastman Chemical Company, Kingsport, Tenn.) are also contemplated to be useful in some embodiments.

In some embodiments, the composition is formulated as a thickened composition, comprising from about 100 □g to about 500 □g of a compound of Formula I or a therapeutically equivalent dose of a compound of Formula I, a polysorbate base, a pharmaceutically acceptable viscosity agent, and water for injection, the concentration of viscosity in the water being sufficient to provide the gel composition with a final viscosity from about 100 to about 50,000 cP. In certain embodiments, the viscosity of the gel is in the range from about 100 to about 10,000 cP, about 200 cP to about 1,000 cP, about 250 cP to about 350 cP, about 300 to about 320 cP. In other embodiments, when an even more viscous medium is desired, the biocompatible gel comprises at least about 65%, at least about 70%, at least about 75%, or even at least about 80% or so by weight of the compound of Formula I. In highly concentrated samples, the biocompatible thickened composition comprises at least about 85%, at least about 90% or at least about 95% or more by weight of the FVIIa modulator.

Suitable bases for use in a thickened composition comprising a compound of Formula I include, but are not limited to, any pharmaceutically acceptable solvent. For example, suitable solvents include polyalkylene glycols such as, but not limited to, polyethylene glycol (PEG) and any combinations or mixtures thereof. In other embodiments, the base is a combination of a pharmaceutically acceptable surfactant and solvent.

In some embodiments, other bases include, sodium stearyl fumarate, diethanolamine cetyl sulfate, isostearate, polyethoxylated castor oil, benzalkonium chloride, nonoxyl 10, octoxynol 9, sodium lauryl sulfate, sorbitan esters (sorbitan monolaurate, sorbitan monooleate, sorbitan monopalmitate, sorbitan monostearate, sorbitan sesquioleate, sorbitan trioleate, sorbitan tristearate, sorbitan laurate, sorbitan oleate, sorbitan palmitate, sorbitan stearate, sorbitan dioleate, sorbitan sesqui-isostearate, sorbitan sesquistearate, sorbitan triisostearate), lecithin pharmaceutical acceptable salts thereof and combinations or mixtures thereof.

In further embodiments, the base is polyethylene glycol. Polyethylene glycol is available in many different grades having varying molecular weights. For example, polyethylene glycol is available as PEG 200; PEG 300; PEG 400; PEG 540 (blend); PEG 600; PEG 900; PEG 1000; PEG 1450; PEG 1540; PEG 2000; PEG 3000; PEG 3350; PEG 4000; PEG 4600 and PEG 8000. For purposes of the present disclosure, all grades of polyethylene glycol are contemplated for use in preparation of a stock of a compound of Formula I. In some embodiments the polyethylene glycol used to prepare a stock of a compound of Formula I is PEG 300.

In other embodiments, the base is a polysorbate. Polysorbates are nonionic surfactants of sorbitan esters. Polysorbates useful in the present disclosure include, but are not limited to polysorbate 20, polysorbate 40, polysorbate 60, polysorbate 80 (Tween 80) and any combinations or mixtures thereof. In further embodiments, polysorbate 80 is utilized as the pharmaceutically acceptable base.

In some embodiments, a water-soluble glycerin-based thickened compositions utilized in the preparation of pharmaceutical delivery vehicles that comprise at least one compound of Formula I contains at least about 0.1% of the water-soluble glycerin compound or more. In some embodiments, the percentage of a compound of Formula I is varied between about 1% and about 95%, between about 5% and about 80%, between about 10% and about 60% or more of the weight or volume of the total pharmaceutical FVIIa modulator composition. In some embodiments, the amount of the gel compound(s) in each therapeutically useful composition is prepared in such a way that a suitable dosage will be obtained in any given unit dose of the compound. Factors such as solubility, bioavailability, biological half-life, route of administration, product shelf life, as well as other pharmacological considerations are contemplated herein and the preparation of such pharmaceutical compositions is presented herein.

In some embodiments, the composition further comprises one or more lipid complexes, liposomes, nanocapsules, microspheres, or other agents which enhances or facilitates the pharmacokinetics of the FVIIa modulator. In other embodiments, the compositions of the present disclosure are formulated and intended for use in therapy, particularly in the therapy of mammals, including humans, domesticated livestock, and animals under the care of a veterinarian or other trained animal medicine practitioner, that have, are suspected of having, or are at risk for developing one or more diseases, disorders, or dysfunctions, including for example, cancerous tumors.

In some embodiments, a single gel composition is used, in which at least one FVIIa modulator is present, while in other embodiments, a pharmaceutical composition that comprises a mixture of two or more distinct gel compositions is used, in which at least one FVIIa modulator is present. In some embodiments, combinations of sols, gels and/or biocompatible matrices is also employed to provide desirable characteristics of FVIIa modulator compositions. In certain embodiments, the gel compositions are cross-linked by one or more agents to alter or improve the properties of the FVIIa modulator.

In one embodiment, combinations of one or more erosion facilitators with one or more diffusion facilitators are also used in the present compositions.

Methods of Preparing

Disclosed herein, in some embodiments, is a method of formulating a composition comprising a compound of Formula I, comprising mixing an aqueous solution of a compound of Formula I:

(Formula I)

with a buffer and one or more pH adjusting agents and adjusting the pH of the composition until the pH of the composition is between about 8.0 and 9.5.

In some embodiments, the buffer is alkali phosphates, or salts of organic acids, inorganic acids or amino acids. In some embodiments, the buffer is citrate, carbonate, acetate, phosphate, triethanolamine, tromethamine, and glutamate. In some embodiments, the buffer is tromethamine.

In some embodiments, the pH adjusting agent is a base, an acid, or combinations thereof. In some embodiments, the base is a solution of sodium hydroxide. The sodium hydroxide solution for pH titration was prepared by dissolving the appropriate amount of sodium hydroxide, NF in Sterile Water for Injection, USP to achieve a 2 N solution. In some embodiments, the acid is a solution of hydrochloric acid. The hydrochloric acid solution for pH titration was prepared by mixing hydrochloric acid, NF with Sterile Water for Injection, USP to achieve a 1 N solution.

In some embodiments, the composition is prepared by dissolving sodium hydroxide, NF and tromethamine, USP in Sterile Water for Injection, USP. In some embodiments, a compound of Formula I is added to the sodium hydroxide and tromethamine solution in portions to avoid clumping. In some embodiments, the pH is adjusted after each portion of drug substance is added by dropwise addition of a 2 N sodium hydroxide solution.

In some embodiments, the pH of the final composition is measured and adjusted with the sodium hydroxide or hydrochloric acid solutions to bring the pH within about 8.2 and about 9.3. In some embodiments, the pH is adjusted to between about 8.4 and 9.1. In some embodiments, the pH is adjusted to about 8.5 and 9.0. In some embodiments, the pH is adjusted to between about 8.6 and 8.9. In some embodiments, the composition is brought to final weight with Sterile Water for Injection, USP In some embodiments, the concentration of the compound of Formula I is greater than about 30 mg/mL. In some embodiments, the concentration of the compound of Formula I is greater than about 60 mg/mL. In some embodiments, the concentration of the compound of Formula I is greater than about 90 mg/mL. In some embodiments, the concentration of the compound of Formula I is about 120 mg/mL.

Routes of Administration

The compositions described herein are formulated for administration to an individual via any conventional means including, but not limited to, subcutaneous, other parenteral (e.g., intravenous, or intramuscular), or transdermal administration routes.

In some embodiments, the compositions described herein are formulated for subcutaneous administration.

In some embodiments, the compositions described herein comprise physiologically acceptable sterile aqueous or non-aqueous solutions, dispersions, suspensions or emulsions, and sterile powders for reconstitution into sterile injectable solutions or dispersions. In some embodiments, compositions described herein comprise water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

In some embodiments, the compositions described herein contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. In further embodiments, it is also be desirable to include isotonic agents, such as sugars, sodium chloride, and the like.

Prolonged absorption of the injectable pharmaceutical form can be brought about by the use of agents delaying absorption, such as aluminum monostearate and gelatin. FVIIa modulator suspension compositions designed for extended release via subcutaneous or intramuscular injection avoid first pass metabolism and lower dosages of the compound of Formula I described herein will be necessary to maintain plasma levels of about 50 ng/ml. In such compositions, the particle size of the compound of Formula I particles and the range of the particle sizes of the compound of Formula I particles are used to control the release of a compound of Formula I by controlling the rate of dissolution in fat or muscle.

In one embodiment, for subcutaneous injections, compounds described herein are formulated in aqueous solutions, in physiologically compatible buffers such as Hank's solution, Ringer's solution, or physiological saline buffer. In some embodiments, for subcutaneous injections, appropriate compositions include aqueous or nonaqueous solutions, with physiologically compatible buffers or excipients.

In other embodiments the compositions are stable under the conditions of manufacture and storage and are preserved against the contaminating action of microorganisms, such as bacteria and fungi. In further embodiments, the carrier is a solvent or dispersion medium containing, for example, water, ethanol, polyol (e.g., glycerol, propylene glycol, and liquid polyethylene glycol, and the like), suitable mixtures thereof, and/or vegetable oils. In other embodiments proper fluidity is maintained, for example, by the use of a coating, such as lecithin, by the maintenance of the required particle size in the case of dispersion and by the use of surfactants. In some other embodiments, the prevention of the action of microorganisms are brought about by various antibacterial and antifungal agents, for example, parabens, chlorobutanol, phenol, sorbic acid, thimerosal, and the like. In other embodiments, the compositions comprise isotonic agents, for example, sugars or sodium chloride. In further embodiments, prolonged absorption of the injectable compositions is brought about by the use in the composition of agents delaying absorption, for example, aluminum monostearate and gelatin.

In some embodiments, a sterile aqueous medium is employed. By way of example only, in one embodiment, a compound of Formula I is dissolved in 1 ml of isotonic NaCl solution and added to 1000 ml of hypodermoclysis fluid or injected at the proposed site of infusion, (see for example, "Remington's Pharmaceutical Sciences" 15th Edition, pages 1035-1038 and 1570-1580). In some embodiments, variation in dosage is dependent on the condition of the individual being treated. In other embodiments, the person responsible for administration will, in any event, determine the appropriate dose for the individual individual. Moreover, in other embodiments, are compositions for human administration wherein preparations meet sterility, pyrogenicity, and the general safety and purity standards as required by FDA Office of Biologics standards.

In other embodiments, the compositions described herein are administered to the desired site, e.g., via injection, infiltration, instillation, implantation, irrigation, or combinations thereof. Administration by any of these methods includes the use of a delivery system such as by way of example an application device such as, but not limited to, a syringe, a tube, and/or a sterile pad (e.g., gauze).

In some embodiments, parenteral administration comprises a bolus injection or a continuous infusion. In another embodiment, compositions for injection are presented in unit dosage form, e.g., in ampoules or in multi-dose containers, with an added preservative. In one embodiment, the pharmaceutical composition described herein is in a form suitable for parenteral injection as a sterile suspensions, solutions or emulsions in oily or aqueous vehicles, and contains formulatory agents such as suspending, stabilizing and/or dispersing agents. In one embodiment, the compound of Formula I is in an injectable composition.

Pharmaceutical compositions for parenteral administration include aqueous solutions of the active compounds in water-soluble form. Additionally, in other embodiments, suspensions of the active compounds are prepared as appropriate oily injection suspensions. Suitable lipophilic solvents or vehicles include fatty oils such as sesame oil, or synthetic fatty acid esters, such as ethyl oleate or triglycerides, or liposomes. In further embodiments, aqueous injection suspensions contain substances which increase the viscosity of the suspension, such as sodium carboxymethyl cellulose, sorbitol, or dextran. In yet a further embodiment, the suspension also contains suitable stabilizers or agents which increase the solubility of the compounds to allow for the preparation of highly concentrated solutions. In another embodiment, the active ingredient is in powder form for constitution with a suitable vehicle, e.g., sterile pyrogen-free water, before use.

In one embodiment, administration of the compound occurs in a local rather than systemic manner, for example, via injection of the compound directly into a particular muscle tissue or an organ, often in a depot preparation or sustained release composition. In some embodiments, such long acting compositions are administered by implantation (for example subcutaneously or intramuscularly) or by intramuscular injection. Furthermore, in other embodiments, administration of a compound of Formula I occurs in a targeted drug delivery system, for example, in a liposome coated with organ-specific antibody. In some other embodiment, the liposomes are targeted to and taken up selectively by the organ. In a further embodiment, the drug is provided in the form of a rapid release composition, in the form of an extended release composition, or in the form of an intermediate release composition.

In some embodiments, transdermal compositions described herein are administered using a variety of transdermal delivery devices. In some embodiments, the transdermal delivery device used with the FVIIa modulator compositions described herein comprise a power source, radio frequency, or a brief electrical current to micro-electrodes in the skin creating "channels" or "pores" in the stratum corneum to facilitate the delivery of the FVIIa modulator composition. In other embodiments, the transdermal delivery device comprises a means for porating the stratum corneum, e.g., microlancing, application of sonic energy, or hydraulic puncturing, to facilitate the delivery of the FVIIa modulator composition. The pores described by the methods herein are typically about 20-50 microns in depth and to not extend into areas of innervation or vascularization.

The transdermal dosage forms described herein incorporate certain pharmaceutically acceptable excipients. In general, the transdermal compositions described herein comprise at least three components: (1) a FVIIa modulator composition; (2) a penetration enhancer; and (3) an aqueous adjuvant. In addition, in some embodiments, transdermal compositions include additional components such as, but not limited to, gelling agents, creams and ointment bases, and the like. In some embodiments, the transdermal composition further comprise a woven or non-woven backing material to enhance absorption and prevent the removal of the transdermal composition from the skin. In other embodiments, the transdermal compositions described herein maintain a saturated or supersaturated state to promote diffusion into the skin.

Another useful composition for administration of compounds having the structure of Formula I employs transdermal delivery devices ("patches"). In some embodiments, such transdermal patches are used to provide continuous or discontinuous infusion of the compound of Formula I in controlled amounts. The construction and use of transdermal patches for the delivery of pharmaceutical agents is described herein. In further embodiments, such patches are constructed for continuous, pulsatile, or on demand delivery of pharmaceutical agents. Still further, transdermal delivery of the compounds of Formula I are accomplished by means of iontophoretic patches and the like. In yet a further embodiment, transdermal patches provide controlled delivery of the compounds. The rate of absorption is slowed by using rate-controlling membranes or by trapping the compound within a polymer matrix or gel. Conversely, in other embodiments, absorption enhancers are used to increase absorption. In some embodiments, compositions suitable for transdermal administration are presented as discrete patches and can be lipophilic emulsions or buffered, aqueous solutions, dissolved and/or dispersed in a polymer or an adhesive. In one embodiment, transdermal patches are placed over different portions of the patient's body.

In some embodiments, compositions suitable for transdermal administration of compounds having the structure of Formula I employ transdermal delivery devices and transdermal delivery patches and are lipophilic emulsions or buffered, aqueous solutions, dissolved and/or dispersed in a polymer or an adhesive. In other embodiments, such patches are constructed for continuous, pulsatile, or on demand delivery of pharmaceutical agents. Still further, some embodiments comprise transdermal delivery of the compounds of Formula I accomplished by means of iontophoretic patches and the like. Additionally, in some other embodiments, transdermal patches provide controlled delivery of the compounds Formula I. In further embodiments the rate of absorption is slowed by using rate-controlling membranes or by trapping the compound within a polymer matrix or gel. Conversely, in other embodiments, absorption enhancers are used to increase absorption. In some embodiments, absorption enhancers or carriers includes absorbable pharmaceutically acceptable solvents to assist passage through the skin. For example, transdermal devices in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In some embodiments, the compound of Formula I is dissolved in an absorbable, pharmacologically acceptable solvent to achieve passage through the external body layer. Suitable solvents include alcohols containing two to 10 carbon atoms, such as hexanol, cyclohexanol, benzylalcohol, 1,2-butanediol, glycerol, and amyl alcohol; hydrocarbons having five to 12 carbon atoms such as n-hexane, cyclohexane, and ethyl benzene; aldehydes and ketones having four to 10 carbon atoms such as heptyl aldehyde, cyclohexanone, and benzaldehyde; esters having four to 10 carbon atoms such as amyl acetate and benzyl propionate; ethereal oils such as oil of eucalyptus, oil of rue, cumin oil, limonene, thymol, and 1-pinene; halogenated hydrocarbons having two to eight carbon atoms such as n-hexyl chloride, nhexyl bromide, and cyclohexyl chloride; or mixtures of any of the foregoing solvents. Also, in some embodiments, with a compound of Formula I, simple pharmacologically acceptable derivatives of the compound of Formula I, such as prodrugs, such as ethers, esters, amides, acetals, etc. having the desired absorption property are be prepared and used in practicing the present disclosure. Of course, the derivatives should be such as to convert to the active form of the compound of Formula I within the body through the action of body enzyme assisted transformations, pH, etc.

In certain embodiments, delivery systems for pharmaceutical compounds are employed, such as, for example, liposomes and emulsions. In certain embodiments, compositions provided herein can also include a mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, the compounds described herein are administered topically and can be formulated into a variety of topically administrable compositions, such as solutions, suspensions, lotions, gels, pastes, medicated sticks, balms, creams or ointments. In further embodiments, such pharmaceutical compounds contain solubilizers, stabilizers, tonicity enhancing agents, buffers and preservatives.

In some embodiments, the compounds described herein are also formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Gels are also used to administer drugs topically or into a body cavity, e.g., nasal passage). In addition to other types of topical gel compositions, the FVIIa modulator compositions presented herein are administered intra-operatively to a surgical site, whereby the composition is applied directly to a cut surface of the skin or to the exposed tissue, muscle or tumor site at the surgical site. Accordingly, in some embodiments, the compositions described herein must be suitable (e.g., sterile) for application to an open incision in order to reduce the risk of infection.

In some embodiments, the compositions and methods disclosed herein are used for treatment at a tumor site with an effective amount of a compound of Formula I in a composition. In one embodiment, the methods involve intra-operative administration of an effective amount of a topical FVIIa modulator composition to a surgical site in a human or animal for treating a tumor at a tumor site.

In some embodiments, administration of a single dose of a topical FVIIa modulator gel according to the methods presently described herein minimizes and/or prevents systemic delivery of the FVIIa modulator for the purposes of: a) producing a selective, highly-localized TF-FVIIa complex inhibition in a discrete, localized area responsible for the formation of the tumor at the tumor site for the purpose of reducing or eliminating cancer arising from a discrete locus (i.e., producing cancer cells), and b) minimizing potential adverse consequences of TF-FVIIa complex formation. The inhibition effect provides relief from diseases, conditions, and disorders related to tumor growth for at least about 48 to about 120 hours, from about 10 to about 21 days, from about 4 to about 5 weeks, for at least about 6 to about 8 weeks, for at least about 16 weeks to about 32 weeks, for at least about 52 weeks or more.

III. Methods of Treatment

Disclosed herein, in some embodiments, is a method of modulating a coagulation cascade, comprising administering to a mammal in need thereof a composition comprising a compound of Formula I:
In some embodiments, the composition further comprises a base, a salt thereof, or combinations thereof. In some embodiments, the base is sodium hydroxide. In some embodiments, the composition further comprises a buffer. In some embodiments, the buffer is alkali phosphates, or salts of organic acids, inorganic acids or amino acids. In some embodiments, the buffer is citrate, carbonate, acetate, phosphate, triethanolamine, tromethamine, and glutamate. In some embodiments, the pH between about 8.0 and about 9.5. In some embodiments, the pH is between about 8.2 and 9.3. In some embodiments, the pH is between about 8.4 and 9.1. In some embodiments, the pH is between about 8.5 and 9.0. In some embodiments, the pH is between about 8.6 and 8.9. In some embodiments, the concentration of the compound of Formula I is greater than about 30 mg/mL. In some embodiments, the concentration of the compound of Formula I is greater than about 60 mg/mL. In some embodiments, the concentration of the compound of Formula I is greater than about 90 mg/mL. In some embodiments, the concentration of the compound of Formula I is about 120 mg/mL. In some embodiments, the composition is in the form of a solution. In some embodiments, the solution is an aqueous solution. In some embodiments, the composition forms a gel at about 2° C. to about 8° C. In some embodiments, the compound of Formula I is administered subcutaneously. In some embodiments, the subcutaneous administration is accomplished by means of a syringe. In some embodiments, the gauge of the needle on the syringe is narrower than a 20 gauge needle. In some embodiments, the needle on the syringe is a 28 gauge needle. In some embodiments, the method further comprises administering radiation therapy to the mammal. In some embodiments, the method further comprises administering an additional chemotherapeutic agent to the mammal. In some embodiments, the mammal is human. In some embodiments, the mammal is not a human.

Disclosed herein, in some embodiments, is a method of modulating the coagulation cascade, comprising administering to a mammal a modulator of Factor VIIa wherein the ratio of $C_{max}$, expressed as □g/ml, to $AUC_{(0-\infty)}$, expressed as □g/ml, for the modulator of the Factor VIIa is less than about 1:15. In some embodiments, the modulator of Factor VIIa is administered in the form of a solution. In some embodiments, the solution is an aqueous solution. In some embodiments, the modulator of Factor VIIa is administered subcutaneously. In some embodiments, the modulator of Factor VIIa has a molecular weight less than 1000 amu. In some embodiments, the modulator of Factor VIIa has the structure of Formula I:

Disclosed herein, in some embodiments, is a method of treating a cancer and/or a thromboembolic disorder, comprising administering to a mammal in need thereof a composition comprising compound of Formula I:
In some embodiments, the composition further comprises a base, a salt thereof, or combinations thereof. In some embodiments, the composition further comprises a buffer. In some embodiments, the pH between about 8.0 and about 9.5. In some embodiments, the concentration of the compound of Formula I is about 120 mg/mL. In some embodiments, the composition is in the form of a solution. In some embodiments, the solution is an aqueous solution. In some embodiments, the composition forms a gel at about 2° C. to about 8° C. In some embodiments, the compound of Formula I is administered subcutaneously. In some embodiments, the subcutaneous administration is accomplished by means of a syringe. In some embodiments, the gauge of the needle on the syringe is narrower than a 20 gauge needle. In some embodiments, the needle on the syringe is a 28 gauge needle. In some embodiments, the method further comprises administering radiation therapy to the mammal. In some embodiments, the method further comprises administering an additional chemotherapeutic agent to the mammal. In some embodiments, the mammal is human. In some embodiments, the mammal is not a human.

In some embodiments, the cancer is selected from adrenal cortical cancer, anal cancer, bile duct cancer, bladder cancer, bone cancer, adult CNS brain tumors (including gliomas, astrocytoma, glioblastoma, oligodendroglioma, and meningioglioma), brain metastases, breast cancer, cervical cancer, childhood Non-Hodgkin's lymphoma, colon and rectum cancer, endometrial cancer, esophagus cancer, Ewing's family of tumors, eye cancer, gallbladder cancer, gastrointestinal carcinoid tumors, gastrointestinal stromal tumors, gestational trophoblastic disease, hematological malignancies, Hodgkin's disease, Kaposi'sarcoma, kidney cancer, laryngeal and hypopharyngeal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplastic syndrome, nasal cavity and paranasal cancer, nasopharyngeal cancer, neuroblastoma, oral cavity and oropharyngeal cancer, osteosarcoma, ovarian cancer, pancreatic cancer, parathyroid cancer, penile cancer, pituitary tumor, prostate cancer, retinoblastoma, rhabdomyosarcoma, salivary gland cancer, sarcoma (osteosarcoma and rhabdomyosarcoma), melanoma skin cancer, nonmelanoma skin cancer, stomach cancer, testicular cancer, thymus cancer, thyroid cancer, uterine sarcoma, vaginal cancer, vulvar cancer, and Waldenstrom's macroglobulinemia. Relevant metastatic tumors include bone metastases. brain metastases, liver metastases, lung metastases and soft tissue metastases. In another embodiment, the cancer can be selected from: lung cancer, colorectal cancer, breast cancer, stomach cancer, malignant melanoma, ovarian cancer, and pancreatic cancer.

In some embodiments, the thromboembolic disorder is venous thrombosis (e.g. DVT) and pulmonary embolism, arterial thrombosis (e.g. in myocardial infarction, unstable angina, thrombosis-based stroke and peripheral arterial thrombosis), and systemic embolism usually from the atrium during atrial fibrillation or from the left ventricle after transmural myocardial infarction, or caused by congestive heart failure; prophylaxis of reocclusion (i.e., thrombosis) after thrombolysis, percutaneous trans-luminal angioplasty (PTA) and coronary bypass operations; the prevention of rethrombosis after microsurgery and vascular surgery in general, the prevention or treatment of venous thromboembolism associated with certain types of cancers such as prostate, stomach, colon, breast, ovary, lung, or malignant melanoma.

Disclosed herein, in some embodiments, is a method of modulating tumor angiogenesis, comprising administering to a mammal in need thereof a composition comprising a compound of Formula I:
In some embodiments, the composition is administered at a tumor site. In some embodiments, the composition further comprises a base, a salt thereof, or combinations thereof. In some embodiments, the base is sodium hydroxide. In some embodiments, the composition further comprises a buffer. In some embodiments, the buffer is alkali phosphates, or salts of organic acids, inorganic acids or amino acids. In some embodiments, the buffer is citrate, carbonate, acetate, phosphate, triethanolamine, tromethamine, and glutamate. In some embodiments, the pH between about 8.0 and about 9.5. In some embodiments, the pH is between about 8.2 and 9.3. In some embodiments, the pH is between about 8.4 and 9.1. In some embodiments, the pH is between about 8.5 and 9.0. In some embodiments, the pH is between about 8.6 and 8.9. In some embodiments, the concentration of the compound of Formula I is greater than about 30 mg/mL. In some embodiments, the concentration of the compound of Formula I is greater than about 60 mg/mL. In some embodiments, the concentration of the compound of Formula I is greater than about 90 mg/mL. In some embodiments, the concentration of the compound of Formula I is about 120 mg/mL. In some embodiments, the composition is in the form of a solution. In some embodiments, the solution is an aqueous solution. In some embodiments, the composition forms a gel at about 2° C. to about 8° C. In some embodiments, the compound of Formula I is administered subcutaneously. In some embodiments, the subcutaneous administration is accomplished by means of a syringe. In some embodiments, the gauge of the needle on the syringe is narrower than a 20 gauge needle. In some embodiments, the needle on the syringe is a 28 gauge needle. In some embodiments, the method further comprises administering radiation therapy to the mammal. In some embodiments, the method further comprises administering an additional chemotherapeutic agent to the mammal. In some embodiments, the mammal is human. In some embodiments, the mammal is not a human.

Further indications include the therapeutic and/or prophylactic treatment of disseminated intravascular coagulation caused by bacteria, multiple trauma, intoxication or any other mechanism; anticoagulant treatment when blood is in contact with foreign surfaces in the body such as vascular grafts, vascular stents, vascular catheters, mechanical and biological prosthetic valves or any other medical device; and anticoagulant treatment when blood is in contact with medical devices outside the body such as during cardiovascular surgery using a heart-lung machine or in haemodialysis; the therapeutic and/or prophylactic treatment of idiopathic and adult respiratory distress syndrome, pulmonary fibrosis following treatment with radiation or chemotherapy, septic shock, septicemia, inflammatory responses, which include, but are not limited to, edema, acute or chronic atherosclerosis such as coronary arterial disease and the formation of atherosclerotic plaques, cerebral arterial disease, cerebral infarction, cerebral thrombosis, cerebral embolism, peripheral arterial disease, ischaemia, angina (including unstable angina), reperfusion damage, restenosis after percutaneous trans-luminal angioplasty (PTA) and coronary artery bypass surgery.

In a further embodiment, any combination of the disorders, diseases and/or conditions listed herein are treated with the compounds provided herein.

VI. Combination Treatments

In some embodiments, the compositions disclosed herein are administered in combination with an additional therapeutic agent. In some embodiments, the compositions and/or agents of the combination therapy are administered concurrently (e.g., simultaneously, essentially simultaneously or within the same treatment protocol) or sequentially, depending upon the nature of the disease, disorder, or condition, the condition of the patient, and the actual choice of compositions and/or agents used.

In some embodiments, the additional therapeutic agent is an additional anti-cancer agent, such as a topical agent, antipruritic agent, mustard application, bone marrow transplant, stem cell transplant, surgery, phototherapy, chemotherapy, photochemotherapy, radiation therapy, immunotherapy, radioimmunotherapy, or systemic therapy.

Examples of such anticancer agents for combination therapies include, e.g., topical steroids, BCNU (Carmustine), nitrogen mustards, photo therapy, topical imiquimod, EBD, MTX, doxorubicin (Doxil), gemcitibine, etoposide, pentostatin, cytokines, interferon, 5-aza-2'-deoxycytidine, all trans retinoic acid, doxorubicin, vincristine, etoposide, gemcitabine, imatinib (Gleevec®), 17-N-Allylamino-17-Demethoxygeldanamycin (17-AAG), flavopiridol, LY294002, bortezomib, trastuzumab, BAY 11-7082, PKC412, or PD184352 in any combination.

Other examples of anticancer agents for combination therapies include Taxol™, also referred to as "paclitaxel", an anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules, and in some embodiments are useful for treating cancer in combination with the compounds described herein.

Other examples of anti-cancer agents for combination therapies include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine hydrochloride; hydroxyurea; idarubicin hydrochloride; ifosfamide; iimofosine; interleukin I1 (including recombinant interleukin II, or r1L2), interferon alfa-2a; interferon alfa-2b; interferon alfa-n1; interferon alfa-n3; interferon beta-1a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other examples of anti-cancer agents for combination therapies include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrapholide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF modulator; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived modulator; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor modulator; interferon agonists; interferons; interleukins; iobenguane; iododoxorubicin; ipomeanol, 4-; iroplact; irsogladine; isobengazole; isohomohalicondrin B; itasetron; j asplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF modulator; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene modulator; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine;

napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator modulator; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C modulator; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP modulator; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived modulator 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell modulator; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other examples of anticancer agents for combination therapies include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, ete.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful as anticancer for combination therapies include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents for combination therapies include, but are not limited to, nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, ete.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin.

Examples of hormones and antagonists useful as anticancer agents for combination therapies include, but are not limited to, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other examples of anticancer agents that can be used in in combination with a composition containing a selective HDAC8 inhibitor include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules for combination therapies include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone, Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser-.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCl), Resverastatin phosphate sodium, BPR-OY-007 (National Health Research Institutes), and SSR-250411 (Sanofi).

In some embodiments, the additional therapeutic agent is an additional anticoagulant. In some embodiments, the anticoagulant is a thrombin modulator, a factor IXa modulator, a factor Xa modulator, or combinations thereof. In some embodiments, the thrombin modulator is Inogatran®, Melagatran® or prodrugs thereof. In some embodiments, the Factor Xa modulator is described in *Current Opinion in Therapeutic Patents*, 1993, 1173-1179 (which is hereby incorporated by reference for such disclosures); 4-{4-[4-(5-chloroindol-2-ylsulfonyl) piperazine-1-carbonyl]phenyl}-pyridine-1-oxide; antistatin; a tick anticoagulant peptide (TAP); SQ-311; SQ-315; SN-292; SN-429; SN 116; RPR-208707; XU-817; SF-324; SF-303; YM 60828; FACTOREX; SF-324; DX9065A; 1-(4-carbamimidoylbenzyl)-4-(6-chloronaphthalene-2-ylsulfonyl)-piperazin-2-one; M55555; DPC423 (1-(3-carbamimidoylphenyl)-2-(2'-aminolsulfonyl [1,1'-biphenyl]-4-ylaminocarbonyl)-4-bromopyrrole, 3-(3,5-difluoro-6-[3-(4,5-dihydro-1-methylimidazol-2-yl)-phenoxy]-4-[2,3-dihydroxy-propoxy]-pyridin-2-yloxy)-4-hydroxybenzamidine; ZK-807834; 1,4-diaza-4-(6-chloronaphthalene-2-ylsulfonyl)-6-(methoxymethyl)-7-oxa-1'-(pyridin-4-yl)spiro[bicyclo-[4.3.0]-nonane-8,4'-piperidine]-2-one; (S)-1-(4-aminoquinazolin-7-ylmethyl)-4-[2-(5-chlorothien-2-yloxy)acetyl]-3-methoxy-methylpiperazin-2-one; 3-(2-[4-(2-aminosulfonyl-phenyl) benzoylphenoxy)-benzamidine; and 4-(2-[4-(5-chloroindol-2-yl-sulfonyl)-2-(pyrrolidin-1-ylcarbonylmethyl)piperazin-1-yl-carbonyl]-thiazol-5-yl)pyridine N-oxide.

In some embodiments, therapeutically effective dosages vary when the compositions are used in treatment combinations. Methods for experimentally determining therapeutically effective dosages of compositions and/or agents for use in combination treatment regimens are described in the literature. For example, the use of metronomic dosing, i.e., providing more frequent, lower doses in order to minimize toxic side effects, has been described extensively in the literature. Combination treatment further includes periodic treatments that start and stop at various times to assist with the clinical management of the patient.

For combination therapies described herein, dosages of the co-administered compositions and/or agents will of course vary depending on the type of co-drug employed, on the specific drug employed, on the disease or condition being treated and so forth. In addition, in some embodiments, when co-administered with one or more biologically active agents, the compound provided herein is administered either simultaneously with the biologically active agent(s), or sequentially. If administered sequentially, the attending physician will decide on the appropriate sequence of administering protein in combination with the biologically active agent(s).

In any case, in other embodiments, the multiple compositions and/or agents (one of which is a compound of Formula I) is administered in any order or even simultaneously. If simultaneously, the multiple therapeutic agents are provided in a single, unified form, or in multiple forms. In further embodiments, one of the therapeutic agents is given in multiple doses, or both are given as multiple doses. If not simultaneous, in other embodiments, the timing between the multiple doses varies from more than zero weeks to less than four weeks. In addition, the combination methods, compositions and compositions are not to be limited to the use of only two agents; the use of multiple therapeutic combinations is also envisioned.

In some embodiments, the agents that make up the combination therapy disclosed herein are in a combined dosage form or in separate dosage forms intended for substantially simultaneous administration. In further embodiments, the agents that make up the combination therapy are also administered sequentially, with either therapeutic agent being administered by a regimen calling for a two-step administration. In yet further embodiments, the two-step administration regimen calls for sequential administration of the active agents or spaced-apart administration of the separate active agents. In one embodiment, the time period between the multiple administration steps ranges from, a few minutes to several hours, depending upon the properties of each pharmaceutical agent, such as potency, solubility, bioavailability, plasma half-life and kinetic profile of the pharmaceutical agent. In further embodiments, circadian variation of the target molecule concentration also determines the optimal dose interval.

In some embodiments, the components of the combination therapies are administered before, during or after the occurrence of a disease or condition, and the timing of administering the composition containing a compound of Formula I is varied. Thus, for example, in some embodiments, the compositions are used as a prophylactic and are administered continuously to individuals with a propensity to develop conditions or diseases in order to prevent the occurrence of the disease or condition. In another embodiment, the compositions are administered to a individual during or as soon as possible after the onset of the symptoms. In a further embodiment, the administration of the composition is initiated within the first 48 hours of the onset of the symptoms, within the first 48 hours of the onset of the symptoms, within the first 6 hours of the onset of the symptoms, and within 3 hours of the onset of the symptoms. In yet a further embodiment, the initial administration is via any route practical, such as, for example, an intravenous injection, a bolus injection, infusion over 5 minutes to about 5 hours, a pill, a capsule, transdermal patch, buccal delivery, and the like, or combination thereof. In yet other embodiments, the composition is administered as soon as is practicable after the onset of a disease or condition is detected or suspected, and for a length of time necessary for the treatment of the disease, such as, for example, from about 1 month to about 3 months. In another embodiment, the length of treatment varies for each individual, and the length is determined using the known criteria. For example, the composition containing the compound is administered for at least 2 weeks, about 1 month to about 5 years, and from about 1 month to about 3 years.

V. Kits/Articles of Manufacture

The disclosure also provides kits for diagnosing, preventing, treating or ameliorating the symptoms of a diseases or disorder in a mammal. Such kits generally will comprise one or more of the pharmaceutically acceptable FVIIa modulator compositions as disclosed herein, and instructions for using the kit. The disclosure also contemplates the use of one or more of the compositions, in the manufacture of medicaments for treating, abating, reducing, or ameliorating the symptoms of a disease, dysfunction, or disorder in a mammal, such as a human that has, is suspected of having, or at risk for developing a cancerous tumor or a thromboembolic disorder.

Disclosed herein, in some embodiments, is a device for administering a composition comprising a compound of Formula I:

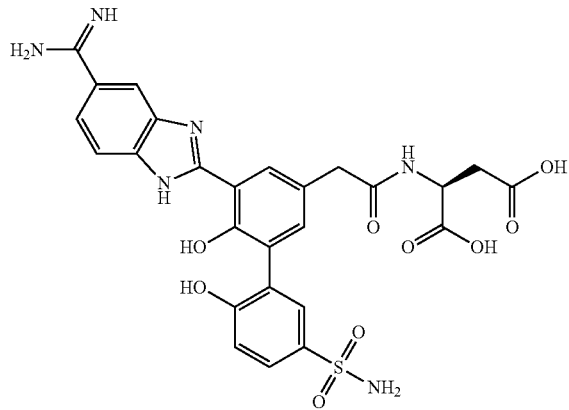

(Formula I)

wherein the device comprises a syringe.

In one embodiment the delivery system is a syringe. In another embodiment, the needle on the syringe is narrower than 20 gauge. In another embodiment, the needle gauge is from 20-33. In a further embodiment, the needle gauge is 28.

In yet another embodiment, the needle is a hypodermic needle used for instant delivery of the compounds and compositions disclosed herein. In a further embodiment, the hypodermic needle is a single use needle.

In yet another embodiment, the needle is a disposable needle.

In some embodiments, is a syringe used for delivery of the compounds and compositions disclosed herein wherein the syringe has a press-fit (Luer) or twist-on (Luer-lock) fitting.

In one embodiment, the syringe is a hypodermic syringe. In yet another embodiment, the hypodermic syringe is a single use syringe.

In a further embodiment, the syringe is a single use syringe.

In another embodiment, the syringe is made of plastic or glass.

In a further embodiment, the glass syringe is capable of being sterilized. In yet a further embodiment, the sterilization occurs through an autoclave.

In another embodiment, the syringe comprises a cylindrical syringe body wherein a compounds and/or composition disclosed herein is stored before use. In other embodiments, the syringe comprises a cylindrical syringe body wherein a compounds and/or composition disclosed herein stored before use which allows for mixing with a suitable pharmaceutically acceptable buffer. In a further embodiment, the syringe contains a stabilizer to stabilize a compound and/or composition disclosed herein. In some embodiments, the syringe comprises a cylindrical syringe body wherein the body is compartmentalized in that each compartment is able to store at least one component of a composition disclosed herein. In a further embodiment, the syringe having a compartmentalized body allows for mixing of the components prior to injection at the tumor site.

In one embodiment is a delivery system wherein the system comprises multiple syringes. In another embodiment, each syringe of the multiple syringes contains at least one component of a composition disclosed herein such that each component can be pre-mixed prior to injection or can be mixed subsequent to injection at the tumor site. In a further embodiment, the syringes disclosed herein comprise at least one reservoir wherein the at least one reservoir comprises a compound of Formula I, or a pharmaceutically acceptable buffer, or a combination thereof.

Commercially available injection devices are employed, in their simplest form as ready-to-use plastic syringes with a syringe barrel, needle assembly with a needle, plunger with a plunger rod, and holding flange, which, as a rule, require skilled handling, especially if a subcutaneous injection is to be performed, i.e., if the needle must first be inserted into a position under the skin that is to be defined as precisely as possible, and only then will the composition be injected. In a further embodiment, the delivery device is suitable for self-administration.

Numerous devices have been developed for injecting medication directly through the skin of a person without requiring a needle or other apparatus for piercing or puncturing the skin. These needleless injection systems use a source of high pressure to force the liquid medication directly through the skin. Various other devices are intended to provide individualized needleless injections. In one embodiment, is a delivery system for delivery of a compound and/or composition disclosed herein without the requirement of a needle.

The present disclosure also provides therapeutic and diagnostic kits that typically comprise one or more of a compound and/or composition disclosed herein and instructions for using the kit in particular regimens or modalities. Likewise, the disclosure provides uses of the compositions in a method for providing a biologically-effective amount of a therapeutic agent to a tumor site of a mammal in need thereof. The method generally involves at least the step of providing a compound and/or composition disclosed herein to a mammal in need thereof in an amount and for a time effective to provide a biologically-effective amount of the therapeutic agent to particular cancerous cells, tissues, or organ(s) of the animal being treated. Modes of administration of the compositions include, for example, systemic administration, or by direct, indirect, or localized injection to a cell, tissue, or organ of the mammal using methodologies described herein.

In some embodiments, kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. In other embodiments, the containers are formed from a variety of materials such as glass or plastic.

The articles of manufacture provided herein contain packaging materials. Packaging materials for use in packaging pharmaceutical products presented herein. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected composition and intended mode of administration and treatment. A wide array of compositions of the compounds and compositions provided herein are contemplated as are a variety of treatments for any disease, disorder, or condition that would benefit by modulation of a coagulation cascade, a FVIIa, and/or a TF-FVIIa complex.

For example, the container(s) include one or more compounds described herein, optionally in a composition or in combination with another agent as disclosed herein. In one embodiment, the container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

In some embodiments, a kit will typically includes one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions will also typically be included.

In a further embodiment, a label is on or associated with the container. In yet a further embodiment, a label is on a container when letters, numbers or other characters forming the label are attached, molded or etched into the container itself; a label is associated with a container when it is present within a receptacle or carrier that also holds the container, e.g., as a package insert. In other embodiments a label is used to indicate that the contents are to be used for a specific therapeutic application. In yet another embodiment, a label also indicates directions for use of the contents, such as in the methods described herein.

In another embodiment, aqueous suspension compositions are packaged in single-dose non-reclosable containers. In a further embodiment, multiple-dose reclosable containers are used, in which case it is typical to include a preservative in the composition.

In certain embodiments, the pharmaceutical compositions are presented in a pack or dispenser device which contains one or more unit dosage forms containing a compound provided herein. In another embodiment, the pack for example contains metal or plastic foil, such as a blister pack. In a further embodiment, the pack or dispenser device is accompanied by instructions for administration. In yet a further embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. In another embodiment, such notice, for example, is the labeling approved by the U.S. Food and Drug Administration for prescription drugs, or the approved product insert. In yet another embodiment, compositions containing a compound provided herein formulated in a compatible pharmaceutical carrier are also prepared, placed in an appropriate container, and labeled for treatment of an indicated condition.

EXAMPLES

The various aspects and advantages of the present disclosure are illustrated by the following non-limiting examples:

Example 1

Lung Colonization by B16F10 Melanoma Cells in Mice

The compound of Formula I (3×50 mg/kg; 3×100 mg/kg) and a control vehicle were administered subcutaneously 1.5 hours before tumor cell inoculation and then at 4.5 hours and 24 hours after tumor cell inoculation. Results showed that in the control vehicle experiment, a substantial number of B16F10 colonies formed in the lung in the majority of the inoculated mice. Results after administration of 3×50 mg/kg showed substantially fewer colonies of B16F10 colonies formed in the lung compared to the control vehicle. Further, following administration of 3×100 mg/kg also showed substantially fewer colonies of B16F10 colonies formed in the lung compared to the control vehicle.

Example 2

Inhibition of Lewis Lung Carcinoma Tumor Growth in C57BL Mice

The compound of Formula I was administered in a gel formulation subcutaneously starting 4 days after tumor cell implantation. Tumor volume in the control experiment continued to increase from about 100 mm$^3$ at 6 days to above 400 mm$^3$ after 13 days and above 500 mm$^3$ after 15 days after start of dosing. 100 mg/kg bid x4d followed by 60 mg/kg bid showed a reduction in the tumor volume of Lewis lung carcinoma tumor in C57BL mice (P<0.01) compared to the control for the 6, 9, 13, and 15 days after the start of dosing. Further, 150 mg/kg bid x4d, then followed by a 90 mg/kg bid, also showed a reduction in the tumor volume of Lewis lung carcinoma tumor in C57BL mice (P≤0.01) compared to the control for the 6, 9, 13, and 15 days after the start of dosing.

Example 3

Figure 6:
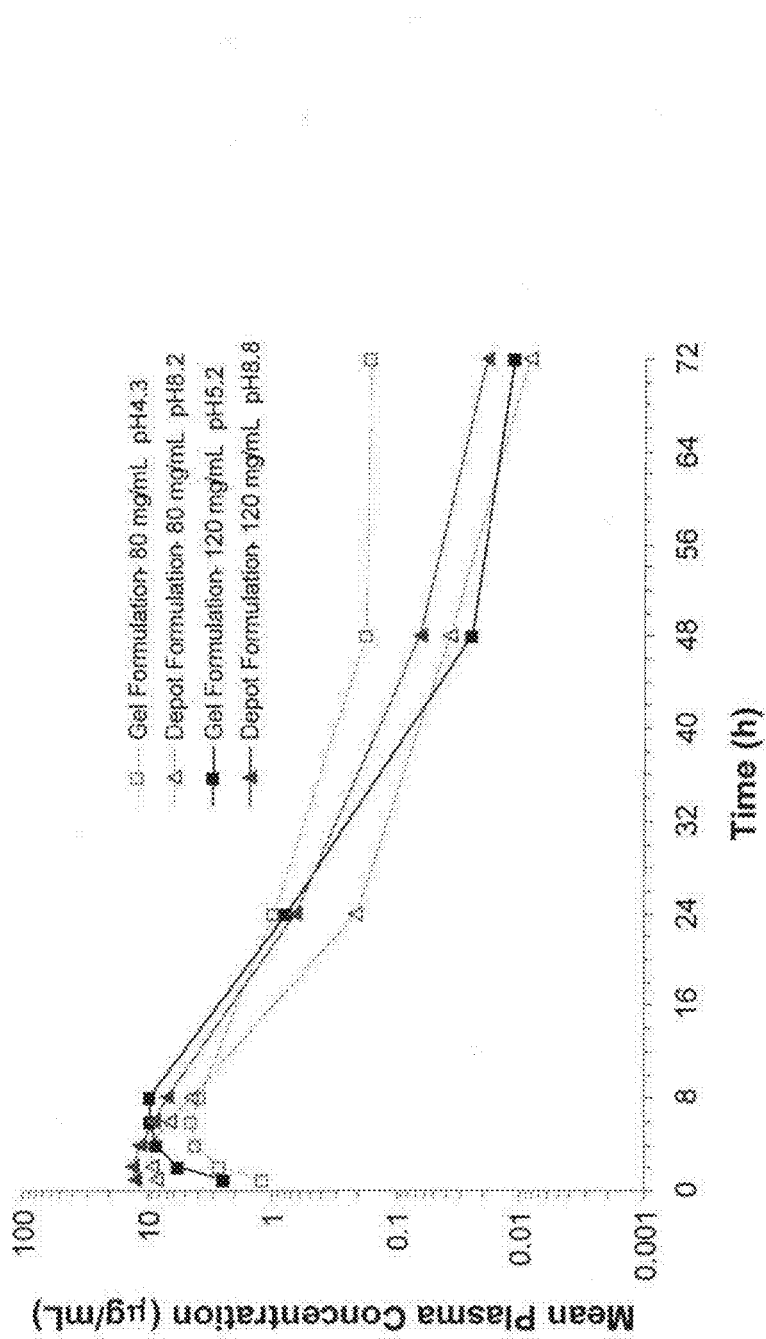
FIG. 6 presents an illustrative graph of the mean plasma concentration of depot and gel compositions in rabbits.

PK of the compound of Formula I Following SC Delivery of Depot and Gel Compositions to Rabbits Shown below in Table 1 are pharmacokinetic data in rabbits for the compound of Formula I following subcutaneous delivery of the FVIIa modulator for both depot and gel compositions to rabbits. Mean Plasma Concentration curves for both the depot and gel compositions at different concentrations and pH are shown in FIG. 6.

TABLE 1

| Group | Formulation | Dose (mg/kg) | $C_{max}$ (µg/mL) | Cmax/ Dose | $T_{max}$ (hr) | $AUC_{0-\infty}$ (µg · hr/mL) | $AUC_{0-\infty}$/ Dose |
|---|---|---|---|---|---|---|---|
| 1 | 80 mg/mL Gel | 16 | 4.71 | 0.29 | 5.33 | 84.71 | 5.29 |
| 2 | 80 mg/mL Depot | 16 | 9.38 | 0.59 | 3.33 | 98.24 | 6.14 |

TABLE 1-continued

| Group | Formulation | Dose (mg/kg) | $C_{max}$ (μg/mL) | Cmax/ Dose | $T_{max}$ (hr) | $AUC_{0-\infty}$ (μg · hr/mL) | $AUC_{0-\infty}/$ Dose |
|---|---|---|---|---|---|---|---|
| 3 | 120 mg/mL Gel | 24 | 10.65 | 0.44 | 7.33 | 148.26 | 6.18 |
| 4 | 120 mg/mL Depot | 24 | 13.23 | 0.55 | 3.33 | 149.68 | 6.24 |
| NA | Baxter Nanoparticle | 12 | 2.62 | 0.22 | 6 | 96.9 | 8.08 |

Example 4

Further Biological Analyses

A study was performed in cynomolgus monkeys with the compound of Formula I to provide information on its pharmacokinetics following intravenous and subcutaneous administration and to determine its subcutaneous bioavailability. The test compound was administered intravenously in a solution (1.76 mg/mL) composition and subcutaneously in a gel composition (107 mg/mL). Following subcutaneous administration in a gel composition (107 mg/mL), The compound of Formula I exhibited a moderate rate of absorption and, on average, reached a maximum plasma concentration 3.33 hours after dosing (shown below in Table 1). The maximum observed plasma concentration ($C_{max}$) following a 10.7 mg/kg subcutaneous dose was 11.6 μg/mL, which was 74% of the $C_{max}$ observed following a 1.76 mg/kg intravenous dose. The terminal half-life following subcutaneous dose administration was 7.43 hours, which was similar to the gamma-phase half-life following intravenous dosing. The subcutaneous bioavailability of the test compound following a single 10.7 mg/kg dose was estimated to be 138±33%. The relative standard deviation for systemic exposure (AUC) following subcutaneous dosing was 20.9% (n=3).

TABLE 2

| | Route of Administration | |
|---|---|---|
| PK Parameter | Intravenous Solution[a] | Subcutaneous Gel[b] |
| $C_{max,obs}$ (μg/mL) | 15.7 (±1.8) | 11.6 (±1.2) |
| $T_{max}$ (h) | — | 3.33 (±1.15) |
| CL (mL/h/kg) | 83.7 (±8.3) | — |
| CL/F (mL/h/kg) | — | 64.3 (±15.0) |
| Vss (L/kg) | 0.430 (±0.044) | — |
| MRT (h) | 5.15 (±0.42) | — |
| $AUC_{0-48}$ (μg · h/mL) | 21.2 (±2.07) | 171 (±35) |
| $AUC_{0-\infty}$ (μg · h/mL) | — | 172 (±36) |
| $t_{1/2\,\alpha}$ (h) | 0.162 (±0.030) | — |
| $t_{1/2\,\beta}$ (h) | 2.19 (±0.13) | — |
| $t_{1/2\,\gamma}$ (h) | 7.07 (±0.53) | — |
| Terminal $t_{1/2}$ (h) | — | 7.43 (±0.18) |
| Bioavailabilty (%) | — | 138 (±33) |

[a]Dosage = 1.76 mg/kg; n = 4.
[b]Dosage = 10.7 mg/kg; n = 3.

Example 5

Figure 7:
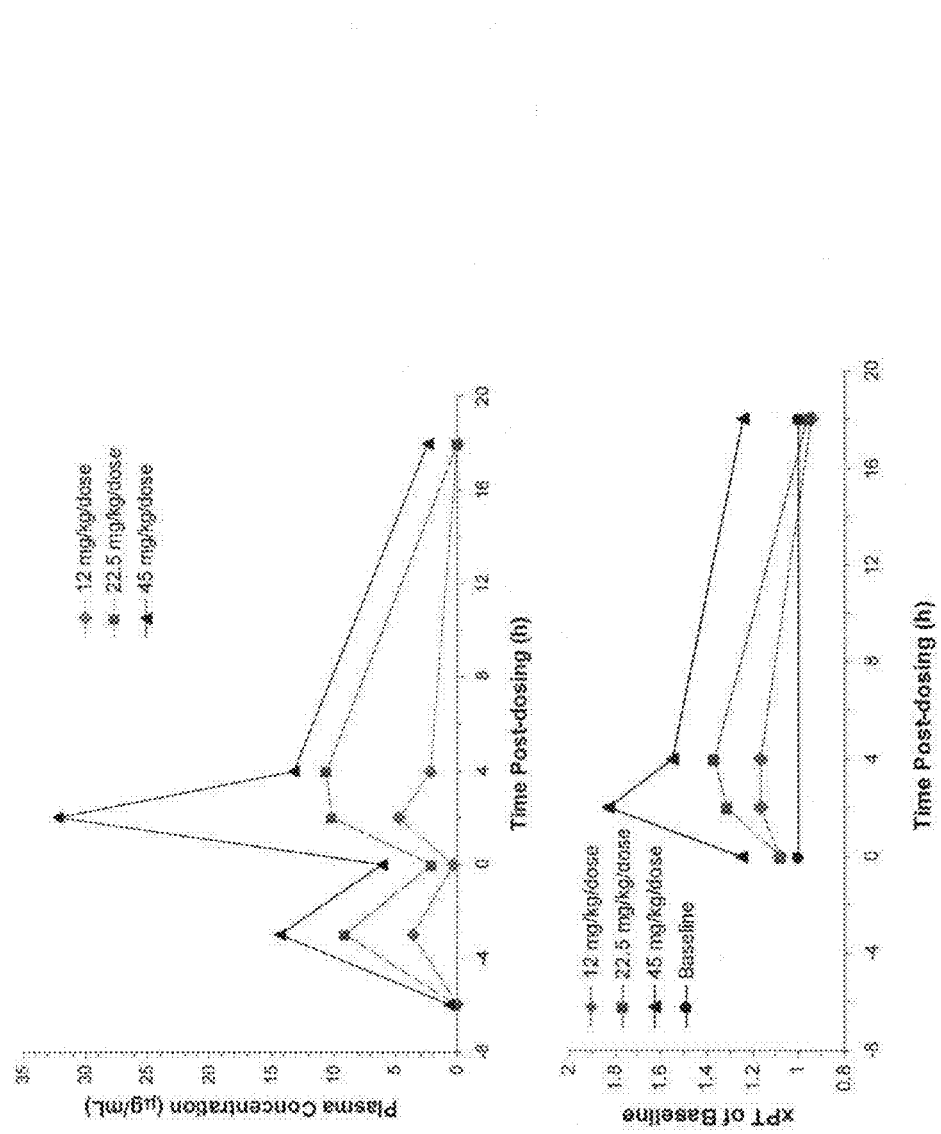
FIG. 7 presents an illustrative study of plasma concentrations of a compound of Formula I and Prothrombin time changes in C57BL/6 mice.
Figure 8:
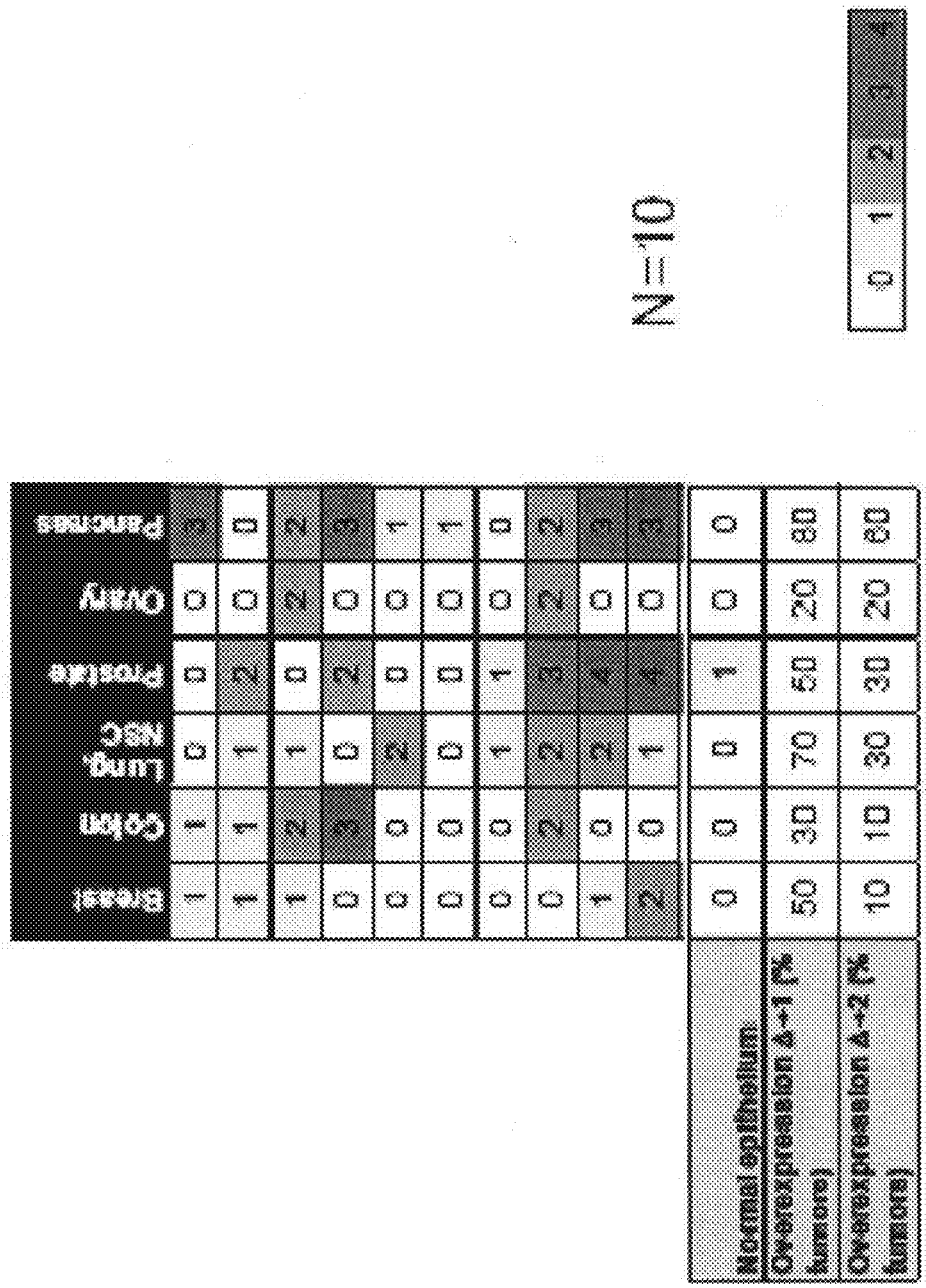
FIG. 8 presents an illustrative IHC data for Tissue Factor Overexpression in Tumors.
Figure 9:
FIG. 9 presents an illustrative example of Factor VIIa as a complex with expressed TF detected in primary pancreatic carcinoma.
Figure 10:
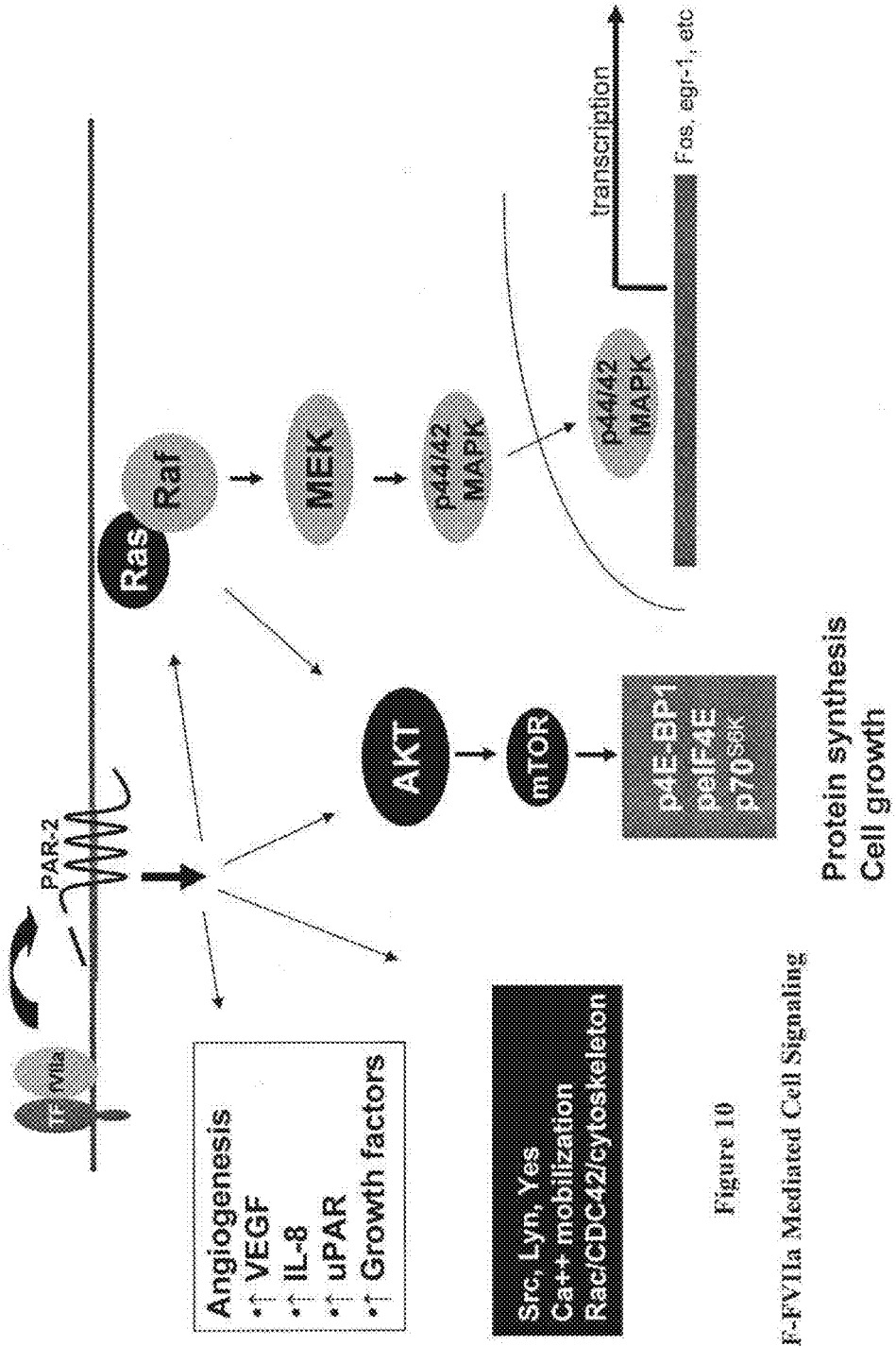
FIG. 10 presents an illustrative model of Tissue Factor-FVIIa mediated cell signaling.

Plasma Concentrations of a Compound of Formula I and Prothrombin Time Changes in C57BL/6 Mice C57BL/6 mice were dosed with a compound of Formula I in a gel composition by subcutaneous injection twice daily for 2 days. Plasma concentrations of a compound of Formula I were measured by LC-MS/MS at select time points following doses 3 and 4. Following drug administration, plasma levels were elevated in a dose dependent manner reaching 15 ug/ml 3 hours after dose 3 at 45 mg/kg/dose. Drug plasma concentrations at all dose levels had dropped significantly by 6 hours after dose 3 but were again elevated in a dose dependent manner following dose 4. Maximal drug plasma levels reached greater than 30 ug/ml 2 hours following dose 4 at 45 mg/kg/dose and dropped to 13 ug/ml by 4 hours post dosing. Drug plasma concentration following dose 4 at 22.5 mg/kg/dose rose to 11 ug/ml at 2 hours and stayed elevated at 4 hours. Drug plasma concentrations for all dose levels were at or near baseline 18 hours following dose 4. Prothrombin (PT) times were measured at 0 (predose), 2, 4, and 18 hours after the 4th dose administration. As shown in FIG. 7, changes in PT times correlated well with changes in drug plasma concentrations with a maximal change in PT time of 1.8 times baseline noted at 2 hours following the 45 mg/kg/dose.

Example 6

Toxicology Studies of a Compound of Formula I

Cynomolgus monkeys were administered a gel formulation of a compound of Formula I twice daily by subcutaneous injection for 28 or 29 consecutive days at a total daily dosage of 0 (vehicle), 3, 12, or 36 mg/kg/day (HED=0.96, 3.84, and 11.5 mg/kg/day, respectively).

Clinical signs noted in the 36 mg/kg/day group males and females included low food consumption; pale body or facial area; and swelling, reddening and scabbing at the dose sites.

One female monkey assigned to the 36 mg/kg/day group had an abnormally high activated partial thromboplastin time (aPTT) value prior to the start of dosing and was euthanized after 3 days of dosing due to severe external hemorrhage.

Lower red blood cell counts, hemoglobin, hematocrit, and mean corpuscular hemoglobin concentration (MCHC) and/or higher reticulocyte counts and/or higher mean corpuscular volume (MCV) were observed in the 12 and 36 mg/kg/day group males and females on study days 14 and 26.

The effects on red blood cell parameters at the 36 mg/kg/day dose level were more pronounced on study day 26 in comparison to study day 14. Compared to values for the control group, the mean red blood cell count at the 36 mg/kg/day dose level was decreased by 39% in males and by 31% in females on study day 14 and by 58% in males and 42% in females on study day 26. Mean red blood cell count at the 12 mg/kg/day dose level was decreased on study day 26 by 8% in males and by 17% in females, when compared to values for the control group.

Histologically, injection sites with subcutaneous hemorrhage and edema increased in severity and incidence in a dose-dependent manner.

The sternum-bone marrow and spleen showed shifts indicative of increased erythropoiesis. The lack of clinical evidence for hemolysis and the brisk erythropoiesis evident in the marrow and blood suggest that the RBC abnormalities observed are due to bleeding.

In males administered 36 mg/kg/day, minimal to mild widening of the interstitium along the medullary rays was noted between distal straight tubules in the kidney medulla.

The NOAEL for subcutaneous administration of a compound of Formula I to monkeys for 28 or 29 consecutive days was 3 mg/kg/day (HED=0.96 mg/kg/day).

Example 7

Manufacture of a Solution Comprising a Compound of Formula I

Step 1. Clean, sterilize, and depyrogenated all equipment and materials, according to the manufacturer's standard procedures, that will come into contact with the components of the composition or the drug product.
Step 2. Prepare the titration buffers.
  a. Add 400 mL of sterile water for injection (SWFI) to a sterile, depyrogenated 1 L glass beaker. Add 40 g of NaOH NF. Add SWFI to a total volume of 500 mL. Add a stir bar and mix until all NaOH is dissolved. Label.
  b. Add 400 mL of SWFI to a sterile, depyrogenated 1 L glass beaker. Add 18.23 g of HCl NF. Add SWFI to a total volume of 500 mL. Add a stir bar and mix until homogeneous. Label.
Step 3. Prepare the composition.
  a. Add 2000 g of SWFI to a new sterile depyrogenated 4 L glass beaker equipped with a sterile, epyrogenated magnetic stir bar.
  b. Start stirring. Set the stirring speed so as to create a slight vortex. Adjust as necessary throughout the process. The solution temperature is controlled to between 20-25° C.
  c. Add 38.4 g of NaOH NF and stir until dissolved.
  d. Add 2.91 g of tromethamine USP and stir until dissolved.
  e. Calculate the total amount of the compound of Formula I to add to achieve a final concentration of 120 mg/mL. Correct for water content and purity per manufacturer's C of A.
  f. Add 50% of the calculated amount of the compound of Formula I. Stir at a rate to keep all undissolved API well suspended. An amber colored solution is obtained.
  g. Insert a new, dedicated and calibrated pH probe into the solution.
  h. Add 20% of the calculated amount of the compound of Formula I. Stir at a rate to keep all undissolved drug substance well suspended.
  i. If, after stirring for 30 minutes, a solution is not obtained and the pH is below pH 10.0, raise the pH of the mixture by adding 2 N NaOH to pH 11.0.
  j. Add 10% of the calculated amount of the compound of Formula I. Stir at a rate to keep all undissolved drug substance well suspended.
  k. If, after stirring for 30 minutes, a solution is not obtained and the pH is below pH 9.0, raise the pH of the mixture by adding 2 N NaOH to pH 10.0.
  l. Add 5% of the calculated amount of the compound of Formula I. Stir at a rate to keep all undissolved drug substance well suspended.
  m. If, after stirring for 30 minutes, a solution is not obtained and the pH is below pH 8.9, raise the pH of the mixture by adding 2 N NaOH close to but not over 8.9.
  n. Add 5% of the calculated amount of the compound of Formula I. Stir at a rate to keep all undissolved drug substance well suspended.
  o. If, after stirring for 30 minutes, a solution is not obtained and the pH is below pH 8.9, raise the pH of the mixture by adding 2 N NaOH close to but not over 8.9.
  p. Add 5% of the calculated amount of the compound of Formula I. Stir at a rate to keep all undissolved drug substance well suspended.
  q. If, after stirring for 30 minutes, a solution is not obtained and the pH is below pH 8.9, raise the pH of the mixture by adding 2 N NaOH close to but not over 8.9.
  r. Add 5% of the calculated amount of a composition comprising a compound of Formula I. Stir at a rate to keep all undissolved drug substance well suspended.
  s. If, after stirring for 30 minutes, a solution is not obtained and the pH is below pH 8.9, raise the pH of the mixture by adding 2 N NaOH close to but not over 8.9.
Step 4: Final adjustments to the composition
  a. Adjust the pH to 8.6-8.9 with the 2 N NaOH or 1 M HCl.
  b. Bring the solution to a final weight of 2568 g (2400 mL) with SWFI.
  c. Dispense 1.2 mL of drug product into each sterile depyrogenated vial. Stopper each vial. Crimp seal each vial. Inspect each capped vial for major defects such as cracked glass or unevenly applied seals. Inspect each vial for particulate matter. Affix an appropriate label to each vial. Store vials refrigerated (5±3° C.)

Example 8

Animal Trials for Central Nervous System (CNS) Responses to Compounds of Formula I To evaluate potential central nervous system (CNS) pharmacological responses to a compound of Formula I, rats in 4 groups of 6 males each received a single dose injection of a composition as described in Example 7. Doses were administered as subcutaneous injections at dose levels of 0 (vehicle), 30, 90, and 240 mg/kg.

Modified functional observational battery and qualitative motor activity data were recorded for all animals 6 days prior to dose administration. Modified functional observational battery and qualitative motor activity data were also recorded beginning approximately 30, 90, 150, 300, and 1440 minutes following dose administration.

No treatment-related toxicity occurred at any dose level.

Example 9

Animal Trials for Respiratory System Responses to Compounds of Formula I

To evaluate potential effects on the respiratory system of a compound of Formula I, rats in 4 groups of 8 males each received a single dose injection of a composition as described in Example 7. Doses were administered as subcutaneous injections at dose levels of 0 (vehicle), 30, 90, and 240 mg/kg.

At the 240 mg/kg dose level, lower tidal volume was observed immediately following dosing to 60 minutes post-dosing (up to 16% lower) and from 226-300 minutes post-dosing (up to 15% lower).

Example 10

Animal Trials for Cardiovascular System Responses to Compounds of Formula I

To evaluate potential effects on the cardiovascular system of a compound of Formula I, cynomolgus monkeys each received ascending single subcutaneous doses of a composition as described in Example 7. Doses were: 0 (vehicle), 3, 12, and 36 mg/kg.

After administration of 36 mg/kg of a composition as described in Example 7, higher heart rate (up to 27% higher) and body temperature (up to 0.4° C. higher) were observed.

Example 11

Animal PK studies

In rats, dogs, monkeys, and baboons, the bioavailability of a compound of Formula I administered subcutaneously in a solution ranged from 95% to 124%.

In dogs, the time to reach maximum plasma concentrations ($T_{max}$) following subcutaneous injection of a compound of Formula I was 0.5 hours.

In baboons, the time to reach maximum plasma concentrations ($T_{max}$) following subcutaneous injection of a compound of Formula I was 2.75 hours.

The terminal half-life ($t_{1/2}$) of a compound of Formula I following subcutaneous administration was 2.67 hours in the rat, 5.68 hours in the dog, 5.40 to 8.14 hours in the monkey, and 7.21 hours in the baboon.

Example 12

Phase I Clinical Trial

Study Objectives

To determine a dose of a composition as described in Example 7 that increases prothrombin time by 2-fold (International Normalized Ratio of Prothrombin Time (INR)=2).
Investigational Drug, Dose, Route, Regimen A composition as described in Example 7 was administered subcutaneously as a single dose regimen as follows: 0.20 mg/kg.

Figure 11:
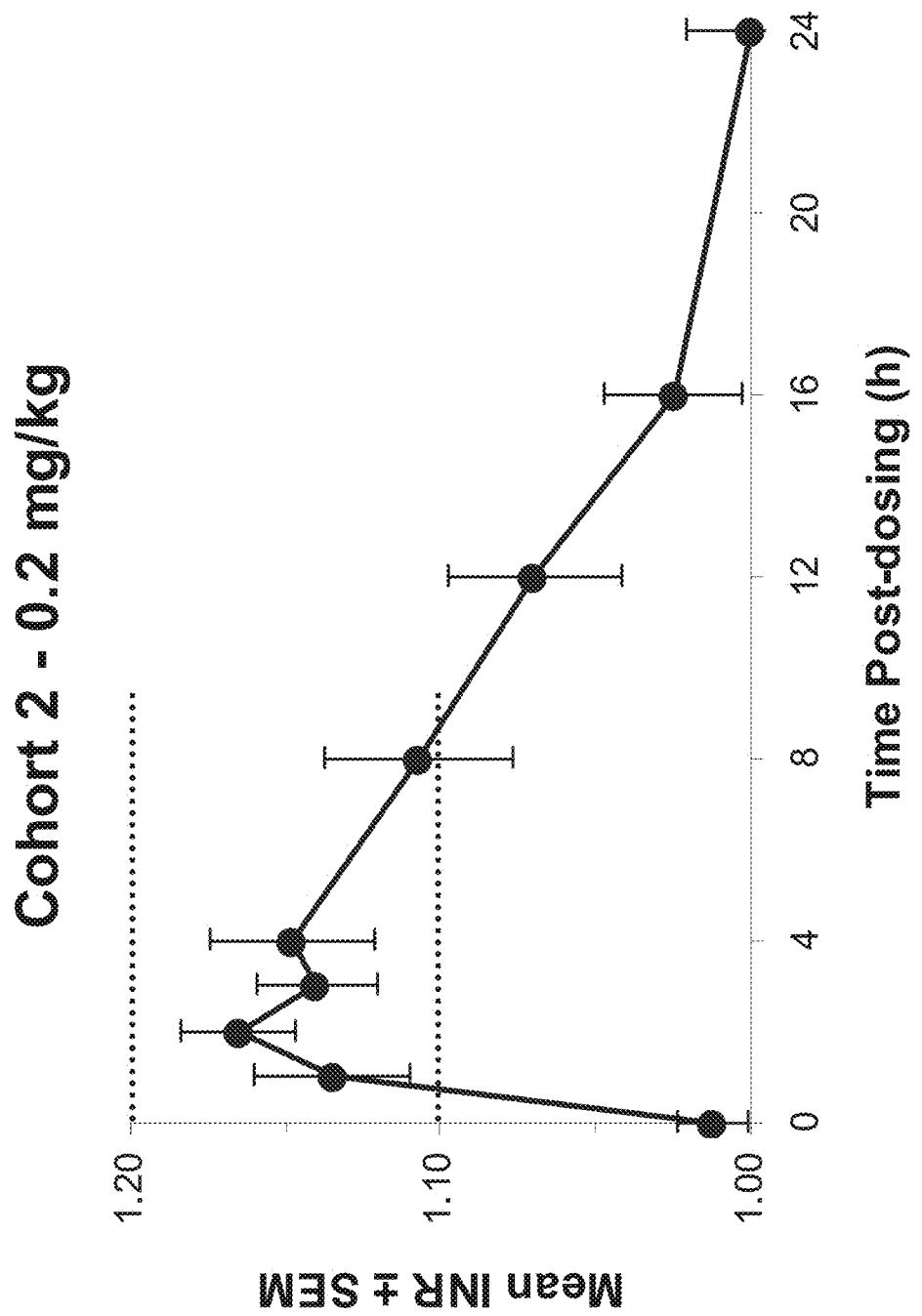
FIG. 11 presents an illustrative graph of pharmacodynamic dose-response achieved in humans.

Results described in FIG. 11.

Example 13

Clinical Trial

Indication: Suppression of tumor growth, metastasis, and angiogenesis in cancers in which progression of disease is dependent on factor VIIa proteolytic activity.
Study Objectives Primary Objective: To determine a pharmacologically effective, single, subcutaneous dose of a composition as described in Example 7 in a cohort mean peak INR (International Normalized Ratio of prothrombin time [PT])≥2.0, or a peak INR≥3.0 for any subject.

Secondary Objectives: To evaluate the safety and tolerability of a single, subcutaneous dose of a composition as described in Example 7, and to determine the pharmacodynamic and pharmacokinetic profiles in healthy adults.
Study Design Phase I, single-center, open-label, dose-escalation study of up to 5 dose-level cohorts of a composition as described in Example 7 administered subcutaneously as a single-dose regimen in healthy adults.

One to 4 healthy adults will be dosed in each sequential cohort after at least 3 days of follow up between cohorts.

In the absence of dose-limiting toxicity (DLT), dose escalation will proceed to the next dose level until a pharmacologically effective dose is determined (cohort mean peak INR≥2.0 or a peak INR≥3.0 for any subject) or the maximum planned dose of 3.0 mg/kg is achieved. If a cohort mean peak INR of ≥1.7 but<2.0 (or an individual peak INR of ≥2.4 but<3.0) is achieved without DLT then escalation to the next dose level may proceed but only at one-half the originally planned dose increment. DLT is defined as the development of any more-than-minimal adverse reactions (ie, any Grade 2 or higher adverse event as defined by the National Cancer Institute Common Terminology Criteria for Adverse Events, version 3.0 [CTCAE]).

To assess the anticoagulation effect that corresponds with the plasma concentrations of a composition as described in Example 7, INR calculated from the PT of each subject will be monitored at baseline, 8 times on Day 1, and daily until the results are within the normal range for a minimum of two consecutive days. If a DLT occurs in 1 of 4 subjects, dosing of additional subjects will proceed upon mutual agreement between the Medical Monitor and the Investigator following review of the event. An additional 1 to 4 subjects may be dosed at that same dose level. Dose escalation will proceed to the next dose level only if no more than 1 of 8 subjects experiences a DLT following the review of safety data by the Medical Monitor and the Investigator. If 2 or more subjects experience a DLT in a single dose level cohort, the previous dose level will be established as the maximum tolerated dose (MTD). If no DLT occurs at any dose, the highest tested dose will be the first dose level of a composition as described in Example 7 that results in a cohort mean peak INR≥2.0 or a peak INR≥3.0 for any subject.

Because human toxicities are not yet defined for this drug and, therefore, attribution to the drug is problematic, all toxicities should be considered as drug-related unless they are clearly not related (eg, environmental). Clinically meaningful toxicity defined by CTCAE and study drug relatedness of adverse events (AEs) will be determined by the principal investigator in consultation with the medical monitor of the study. Any subject who exhibits clinically significant bleeding during the study will undergo detailed investigations of the relevant coagulation factors and platelet function after an appropriate study drug wash-out period.
Study Duration 15±2 days per cohort
Study Population Approximately 20 to 40 healthy adult men or women 18 to 65 years of age (4 to 8 subjects per dose-level cohort).
Study Endpoints:

Primary endpoint
  a. Pharmacologically active dose (defined as the first dose level that results in a cohort mean peak INR≥2.0 or a peak INR≥3.0 for any subject), or MTD and associated DLT (CTCAE Grade≥2 toxicity, regardless of causality)

Secondary Endpoints:
  a. Adverse event profile
  b. Plasma Cmax, Tmax, half-life, and AUC of a composition as described in Example 7
  c. Urinary excretion of a composition as described in Example 7

Investigational Drug, Dose, Route, Regimen

Factor VIIa modulator, a composition as described in Example 7, administered subcutaneously as a single dose regimen in five dose level cohorts as follows: 0.05 mg/kg, 0.20 mg/kg, 0.80 mg/kg, 2.0 mg/kg, and 3.0 mg/kg.
Visit Schedule Screening visit and Study Days 1, 2, 3, and 15±2. Additional days may be required based on laboratory values.
Assessments Safety assessments will consist of adverse events, vital signs, electrocardiograms, laboratory assessments including serum chemistry panel, hematology panel, coagulation panel, and urinalysis), and injection site assessments.

Blood and urine will be collected for pharmacokinetic assessment.

Inclusion Criteria

To be eligible to participate in this study, a subject must meet all of the following criteria:
 a. Healthy woman or man 18 to 65 years of age, inclusive.
 b. Body Mass Index 18.5-30.0 kg/m2 inclusive.
 c. Normal baseline coagulation or deemed not clinically significant by the investigator:
 d. PT 11.5-14.5 seconds and aPTT 22-37 seconds.
 e. Ability to understand the study, willingness to participate in the study, and ability to provide written informed consent to participate.
 f. In good health (ie, no evidence of clinically significant underlying medical condition). Stable, well-controlled hypertension is allowed if not on medication.
 g. Women must be amenorrheic for at least 12 months or have had a total hysterectomy.
 h. Available for follow-up assessments for 15±2 days.
 i. Agree to not participate in contact sports or strenuous activity during the 15±2 day study period.

Exclusion Criteria

A subject meeting any of the following criteria will be excluded from this study:
 a. History of any clinically significant medical condition that, in the opinion of the principal investigator, is defined as "not in good health".
 b. Elective surgery, dental work, or regional anesthesia planned during the trial period.
 c. Known history of clinically significant bleeding after surgery or childbirth (required blood transfusions) or after dental extraction (required suturing).
 d. Known history of clinically significant recurrent bleeding episodes.
 e. Known history of a congenital coagulation factor deficiency.
 f. Known acquired or hereditary platelet disorder.
 g. Known history of immunodeficiency.
 h. Known vascular abnormality.
 i. Any major trauma or surgery within 6 months, or biopsy planned within the study duration.
 j. Ongoing treatment with, or need for, oral antithrombotics including anticoagulants (eg, coumadin) and antiplatelet agents (eg, aspirin).
 k. Sexually active men unwilling to use adequate contraceptive protection or unwilling to refrain from sperm donation for entire duration of the study.
 l. Presence of any acute symptoms of headache, rhinitis, cough, sore throat, fever, nausea, and/or vomiting within 3 days of Study Entry.
 m. Use of aspirin or other nonsteroidal anti-inflammatory agents (NSAIDs) within 14 days of Study Entry, or planned use within the study duration.
 n. Use of alcohol, tobacco, or other drugs (prescription or over-the-counter) within 3 days of Study Entry, or planned use within the study duration.
 o. Uncontrolled hypertension (systolic>160 or diastolic>100).
 p. Positive stool occult blood test.
 q. Chronic active hepatitis B or C, as confirmed by laboratory testing at Screening.
 r. HIV infection, as confirmed by laboratory testing at Screening.
 s. Renal insufficiency (BUN or creatinine>upper limit of normal [ULN]).
 t. Hepatic disease (AST, ALT, alkaline phosphatase, total bilirubin, or GGT>ULN).
 u. Contraindication to systemic anticoagulation.
 v. Anemia (Hgb<12 gm/dL).
 w. Thrombocytopenia (platelet count<150,000/μL).
 x. Hematuria (microscopic).
 y. Participation in any study of an investigational device, medication, biologic, or other agent within 30 days prior to enrollment, or planned participation within the study duration.
 z. Participation in a prior cohort of this study.

The examples and embodiments described herein are for illustrative purposes only and various modifications or changes are to be included within the spirit and purview of this application and scope of the appended claims.

What is claimed is:

1. A solution comprising:
 a) a compound of Formula I or a salt thereof:

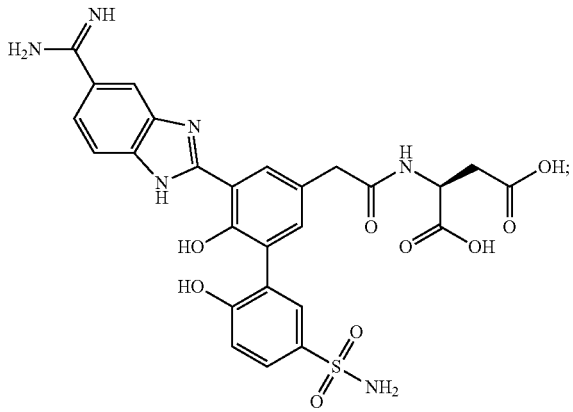

(Formula I)

and
 b) an amino acid buffer;
wherein the compound of Formula I or the salt thereof and the amino acid buffer are in solution.

2. The solution of claim 1, further comprising an additional therapeutic agent, and a pharmaceutically acceptable excipient.

3. The solution of claim 1, further comprising a divalent cation.

4. A solution comprising:
 a) a compound of Formula I or a salt thereof:

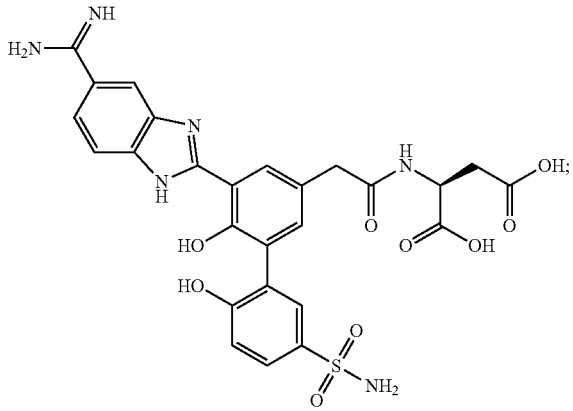

(Formula I)

b) an amino acid buffer;
 c) an additional therapeutic agent;
 d) a divalent cation; and
 e) a pharmaceutically-acceptable excipient;

wherein the compound of Formula I or the salt thereof, the amino acid buffer, the additional therapeutic agent, the divalent cation and the pharmaceutically-acceptable excipient are dissolved in the solution.

* * * * *

UNITED STATES PATENT AND TRADEMARK OFFICE
CERTIFICATE OF CORRECTION

| | | |
|---|---|---|
| PATENT NO. | : 8,748,468 B2 | Page 1 of 1 |
| APPLICATION NO. | : 13/668167 | |
| DATED | : June 10, 2014 | |
| INVENTOR(S) | : David Loury et al. | |

It is certified that error appears in the above-identified patent and that said Letters Patent is hereby corrected as shown below:

In the Specification

Column 1, lines 8-9, delete "This application is a continuation application of U.S. patent application Ser. No. 12/738,372, filed Apr. 16, 2012" and replace with --This application is a continuation application of U.S. patent application Ser. No. 12/738,372, filed July 27, 2010--

Column 8, line 1, delete "expressed as ☐g/ml" and replace with --expressed as µg/ml--; lines 1-2, delete "expressed as ☐g/ml" and replace with --expressed as µg/ml--

Column 13, line 20, delete "typically measured in mg, ☐g, or ng" and replace with --typically measured in mg, µg, or ng--; lines 23-24, delete "typically measured in ☐g/ml" and replace with --typically measured in µg/ml--

Column 24, lines 55-56, delete "from about 100 ☐g to about 500 ☐g of a compound" and replace with --from about 100 µg to about 500 µg of a compound--

Column 32, line 24, delete "expressed as ☐g/ml" and replace with --expressed as µg/ml--; lines 24-25, delete "expressed as ☐g/ml" and replace with --expressed as µg/ml--

Signed and Sealed this
Tenth Day of February, 2015

Michelle K. Lee
*Deputy Director of the United States Patent and Trademark Office*